(12) United States Patent
Carranza et al.

(10) Patent No.: US 7,427,261 B1
(45) Date of Patent: *Sep. 23, 2008

(54) SYSTEM FOR PREPARING A CRAFT VESSEL FOR ANASTOMOSIS

(75) Inventors: Jose R. Carranza, South San Francisco, CA (US); Brendan M. Donohoe, San Francisco, CA (US); Theodore M. Bender, San Francisco, CA (US)

(73) Assignee: Cardica, Inc., Redwood City, CA (US)

( * ) Notice: Subject to any disclaimer, the term of this patent is extended or adjusted under 35 U.S.C. 154(b) by 1307 days.

This patent is subject to a terminal disclaimer.

(21) Appl. No.: 10/426,838

(22) Filed: Apr. 30, 2003

Related U.S. Application Data

(63) Continuation-in-part of application No. 10/055,179, filed on Jan. 23, 2002, now Pat. No. 6,821,286.

(51) Int. Cl.
*A61F 2/04* (2006.01)

(52) U.S. Cl. .................................................... 600/36

(58) Field of Classification Search .................. 600/36; 606/139–142, 149, 151, 153–156, 184, 213, 606/219, 220
See application file for complete search history.

(56) References Cited

U.S. PATENT DOCUMENTS

| | | | |
|---|---|---|---|
| 2,940,452 A | 6/1960 | Smialowski | |
| 3,057,355 A | 10/1962 | Smialowski et al. | |
| 3,180,337 A | 4/1965 | Smialowski | |
| 3,908,662 A | 9/1975 | Razgulov et al. | |
| 4,214,587 A | 7/1980 | Sakura, Jr. | |
| 4,352,358 A | 10/1982 | Angelchik | |
| 4,359,054 A * | 11/1982 | Leist et al. ................ 600/354 |
| 4,366,819 A | 1/1983 | Kaster | |
| 4,470,415 A | 9/1984 | Wozniak | |
| 4,501,363 A | 2/1985 | Isbey et al. | |
| 4,553,542 A | 11/1985 | Schenck et al. | |
| 4,562,596 A | 1/1986 | Kornberg | |
| 4,593,693 A | 6/1986 | Schenck | |
| 4,622,970 A | 11/1986 | Wozniak | |
| 4,624,255 A | 11/1986 | Schenck et al. | |
| 4,674,506 A * | 6/1987 | Alcond ..................... 606/153 |
| 4,711,129 A * | 12/1987 | Stubenberg et al. ......... 73/708 |
| 4,801,299 A | 1/1989 | Brendel et al. | |
| 5,234,447 A | 8/1993 | Kaster et al. | |

(Continued)

FOREIGN PATENT DOCUMENTS

CA    0616611    3/1961

(Continued)

*Primary Examiner*—Samuel G Gilbert
(74) *Attorney, Agent, or Firm*—Brian A. Schar

(57) ABSTRACT

A system for preparing a graft vessel for anastomosis includes one or more tools held within a functional package. The package includes a tray and tray top, either or both of which may include one or more features configured to hold the contents of the tray securely therein, and/or may include one or more registration features configured to register one or more items in a desired position in the tray. The package has multiple recesses for holding one or more tools for preparing a graft vessel for anastomosis, and can be sealed and sterilized along with its contents. One of these tools may be a poke-through tool that includes a plurality of membranes within a shell.

15 Claims, 23 Drawing Sheets

U.S. PATENT DOCUMENTS

| | | | |
|---|---|---|---|
| 5,290,295 A | 3/1994 | Querals et al. | |
| 5,336,233 A * | 8/1994 | Chen | 606/153 |
| 5,366,462 A | 11/1994 | Kaster et al. | |
| 5,424,495 A * | 6/1995 | Wurzburger | 181/131 |
| 5,676,670 A | 10/1997 | Kim | |
| 5,695,504 A | 12/1997 | Gifford, III et al. | |
| 5,707,362 A | 1/1998 | Yoon | |
| 5,769,887 A | 6/1998 | Brown et al. | |
| 5,817,113 A | 10/1998 | Gifford, III et al. | |
| 5,920,038 A * | 7/1999 | Foster | 181/131 |
| 5,957,938 A | 9/1999 | Zhu et al. | |
| 5,976,161 A | 11/1999 | Kirsch et al. | |
| 6,110,191 A | 8/2000 | Dehdashtian et al. | |
| 6,358,258 B1 | 3/2002 | Arcia et al. | |
| 6,402,764 B1 | 6/2002 | Hendricksen et al. | |
| 6,485,496 B1 | 11/2002 | Suyker et al. | |
| 6,494,889 B1 | 12/2002 | Fleischman et al. | |
| 6,547,799 B2 | 4/2003 | Hess et al. | |
| 2004/0002721 A1 | 1/2004 | Podmore et al. | |

FOREIGN PATENT DOCUMENTS

| | | |
|---|---|---|
| WO | 99/62415 | 12/1999 |
| WO | 00/56226 | 9/2000 |
| WO | 01/70119 | 9/2001 |
| WO | WO-01/91628 | 12/2001 |

* cited by examiner

SYSTEM FOR PREPARING A CRAFT VESSEL FOR ANASTOMOSIS

This application is a continuation-in-part of U.S. patent application Ser. No. 10/055,179 filed on Jan. 23, 2002 now U.S. Pat. No. 6,821,286, which is hereby incorporated by reference in its entirety.

FIELD OF THE INVENTION

The present invention relates generally to anastomosis, and more particularly to a set of tools and a functional package for preparing a graft vessel for anastomosis.

BACKGROUND

Anastomosis is a procedure where two separate tubular or hollow organs are surgically grafted together to form a continuous fluid channel between them. Vascular anastomosis involves creating an anastomosis between blood vessels to create or restore blood flow. When a patient suffers from coronary artery disease (CAD), an occlusion or stenosis in a coronary artery restricts blood flow to the heart muscle. In order to treat CAD, the area where the occlusion occurs is bypassed to reroute blood flow by grafting a vessel in the form of a harvested artery or vein, or a prosthesis. Anastomosis is performed between a graft vessel and two target vessels in order to bypass the blocked coronary artery, circumvent the occlusion and restore adequate blood flow to the heart muscle. This treatment is known as a coronary artery bypass graft procedure (CABG).

In a CABG procedure, a graft vessel such as a saphenous vein, mammary artery, radial artery or other blood vessel is harvested from the patient or another source, then placed in a bowl or other container and immersed in saline, blood or other biocompatible liquid. Before that graft vessel is connected to the target vessels, it may be prepared in some way, such as by connecting it to an anastomosis device and/or a tool for applying the anastomosis device.

SUMMARY

A system for preparing a graft vessel for anastomosis includes one or more tools held within a functional package.

In one aspect of the invention, a protection feature is provided in conjunction with an anastomosis tool recess within a tray. The protection feature is located at an end of the anastomosis tool recess configured to receive an operative end of an anastomosis tool. The operative end of the anastomosis tool may include an auger, an anastomosis device, or other sharp or delicate element or elements. The protection feature is positioned to prevent inadvertent contact with the operative end of the anastomosis tool, thereby protecting it from interference and protecting a user's surgical glove and hand from contact with any sharp points or edges of the operative end.

In another aspect of the invention, a working recess in the tray is configured to hold an assembly that includes a cartridge, a crown and an anastomosis device connected to the crown. A support is provided in the working recess, positioned such that the crown contacts the support as the assembly is removed from the working recess. Such contact between the crown and the support substantially prevents contact between the anastomosis device and the tray.

In another aspect of the invention, the working recess includes a stop that engages the cartridge. When a poke-through tool is utilized in conjunction with the assembly, the stop limits or substantially prevents motion of the cartridge relative to the tray as the poke-through tool engages the anastomosis device.

In another aspect of the invention, the tray and/or tray top may include one or more features configured to hold the contents of the tray securely therein. The tray and/or tray top may also, or instead, include one or more registration features configured to register one or more items in a desired position in the tray. In another aspect of the invention, at least one poke-through tool includes a plurality of membranes, for redundancy. At least one reference mark may be present on each membrane. The intersection of these reference marks, when viewed longitudinally with reference to the poke-through tool, can be used to verify proper alignment and positioning of the membranes. Multiple poke-through tools may be provided in association with each anastomosis tool, providing additional redundancy. Each poke-through tool may be held within a separate recess in the tray until removed for use.

In another aspect of the invention, a holder is positioned along a tube of a pull-through tool, where tension members extend through a lumen or opening in the holder. The holder provides closer alignment for grasping elements at the distal end of the tension members as they are moved.

BRIEF DESCRIPTION OF THE DRAWINGS

The use of the same reference symbols in different figures indicates similar or identical items.

DETAILED DESCRIPTION

Figure 1:
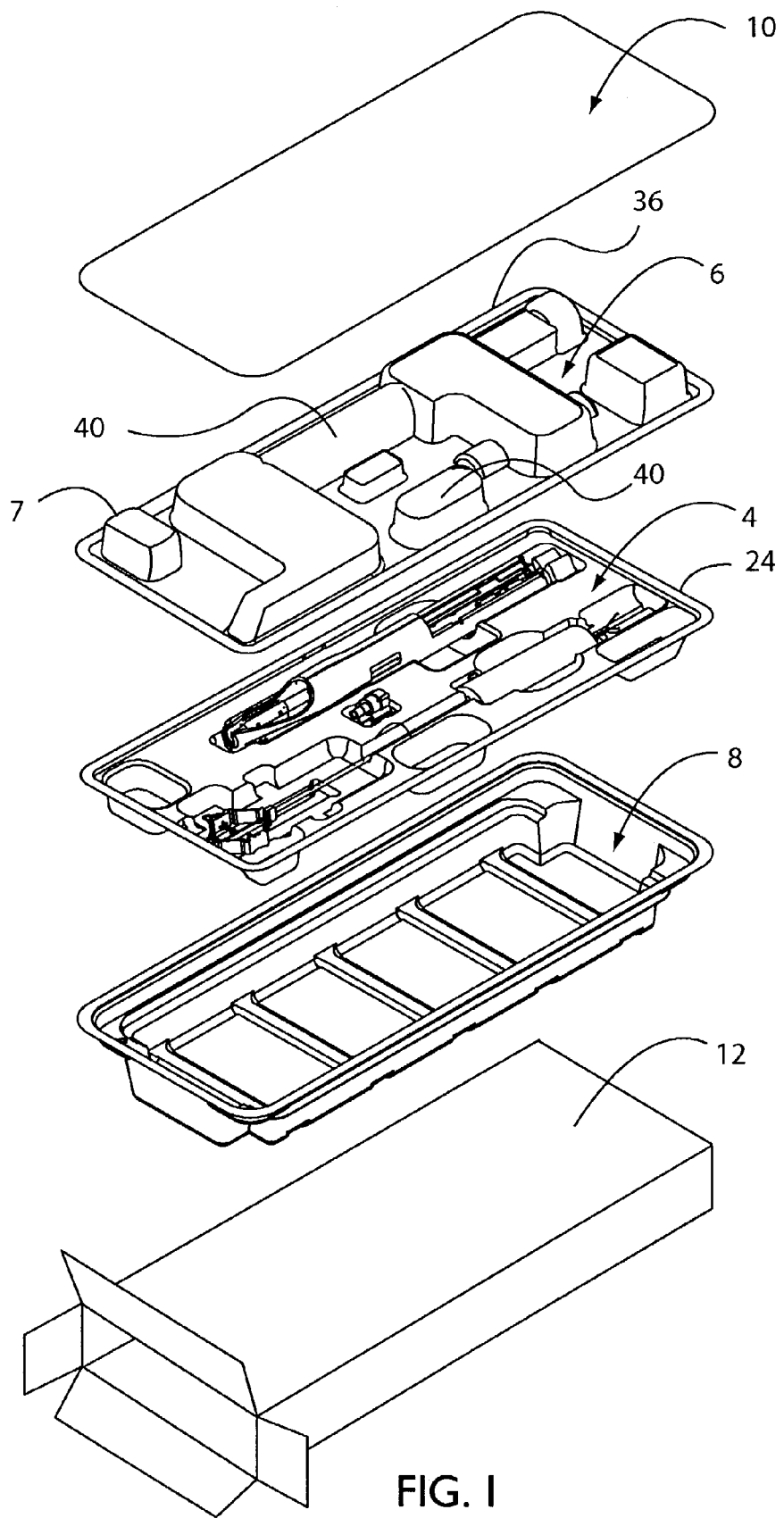
FIG. 1 is an expanded view of the components of a functional package.
Figure 2:
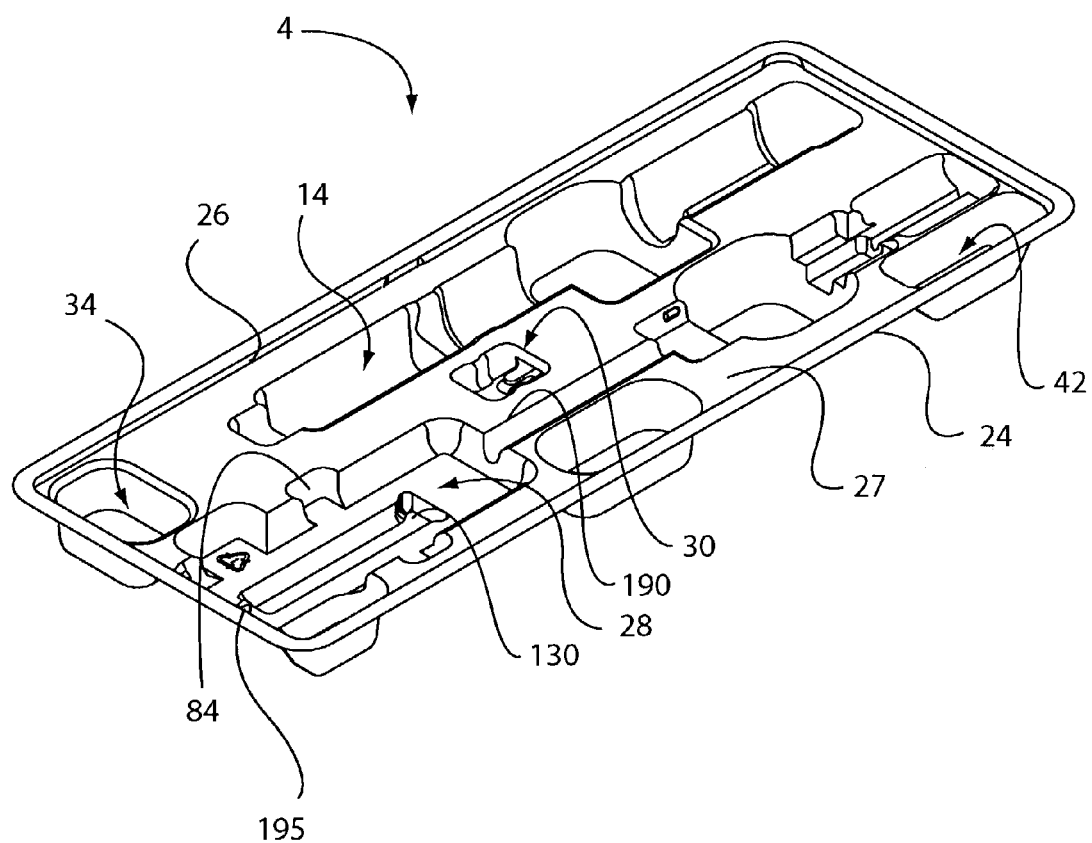
FIG. 2 is a perspective view of a tray that is a component of the functional package of FIG. 1.
Figure 3:
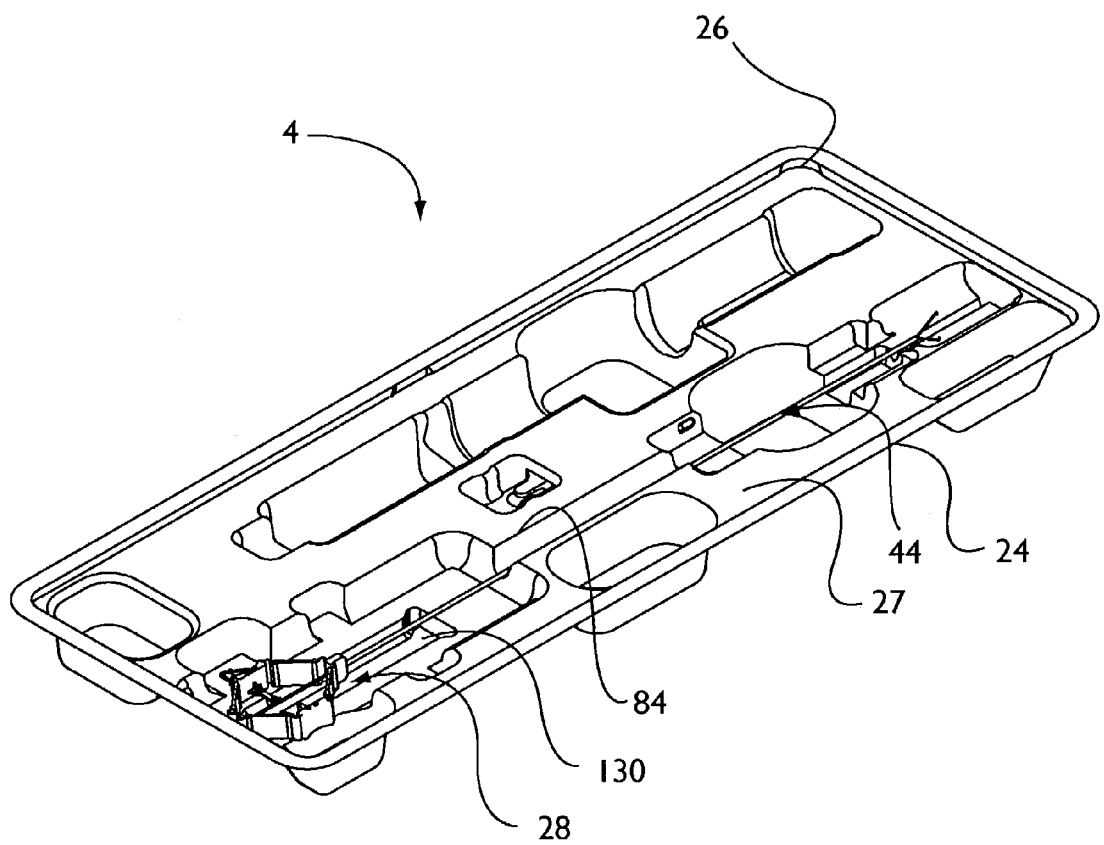
FIG. 3 is a perspective view of the tray of FIG. 2 in which a pull-through tool is held in a recess in the tray.

Referring to FIG. 1, a functional package 2 for preparing a graft vessel for anastomosis is shown. The system includes a tray 4, a tray top 6, an outer shell 8, a cover 10 and an exterior box 12. Referring also to FIGS. 2-3, the tray 4 is shown in greater detail. The tray 4 is constructed from vacuum-formed plastic or other biocompatible material. The tray 4 need not be vacuum-formed, and may be constructed in a different way if desired. A lip 24 extends outward at least partly around the perimeter of the tray 4. The lip 24 is substantially horizontal. Alternately, the lip 24 may be oriented differently in whole or in part. For example, the lip 24 may be angled relative to the horizontal. Alternately, two or more separate lips 24 are provided along portions of the perimeter of the tray 4. The lip 24 extends outward from a ledge 26 that extends at least partly around the perimeter of the tray 4. The ledge 26 extends substantially vertically. Alternately, the ledge 26 may be oriented differently in whole or in part. For example, the ledge 26 may be angled relative to the vertical. Alternately, two or more separate ledges 26 are provided along portions of the perimeter of the tray 4. The ledges 26 extend downward to a surface 27 that is substantially horizontal. The surface 27 may be oriented differently, if desired. A number of recesses are formed into the tray 4, recessed relative to the surface 27. These recesses may be molded into the tray 4, or formed in another way. These recesses may include a working recess 28, a poke-through tool recess 30, an anastomosis tool recess 32, and a stabilizing recess 34. The functions of the recesses 28, 30, 32, 34 are described in greater detail below.

Referring back to FIG. 1, the tray top 6 rests on the tray 4, and may be sealed to it. One or more features 40 are formed into the tray top 6 to provide clearance for tools held in the tray 4. The features 40 may be molded into the tray top 6 or otherwise formed into the tray top 6. The tray top 6 assists in restraining the tools held in the tray and protecting them from contamination. One or more lips 36 extend outward from the perimeter of the tray top 6. The lip 36 of the tray top 6 is constructed to correspond with the lip 24 of the tray. Thus, if the lip 24 of the tray 4 is substantially horizontal, then the lip 36 of the tray top 6 is substantially horizontal. When the tray top 6 is placed on the tray 4, the lip 36 of the tray top 6 contacts the lip 24 of the tray 4.

Figure 4:
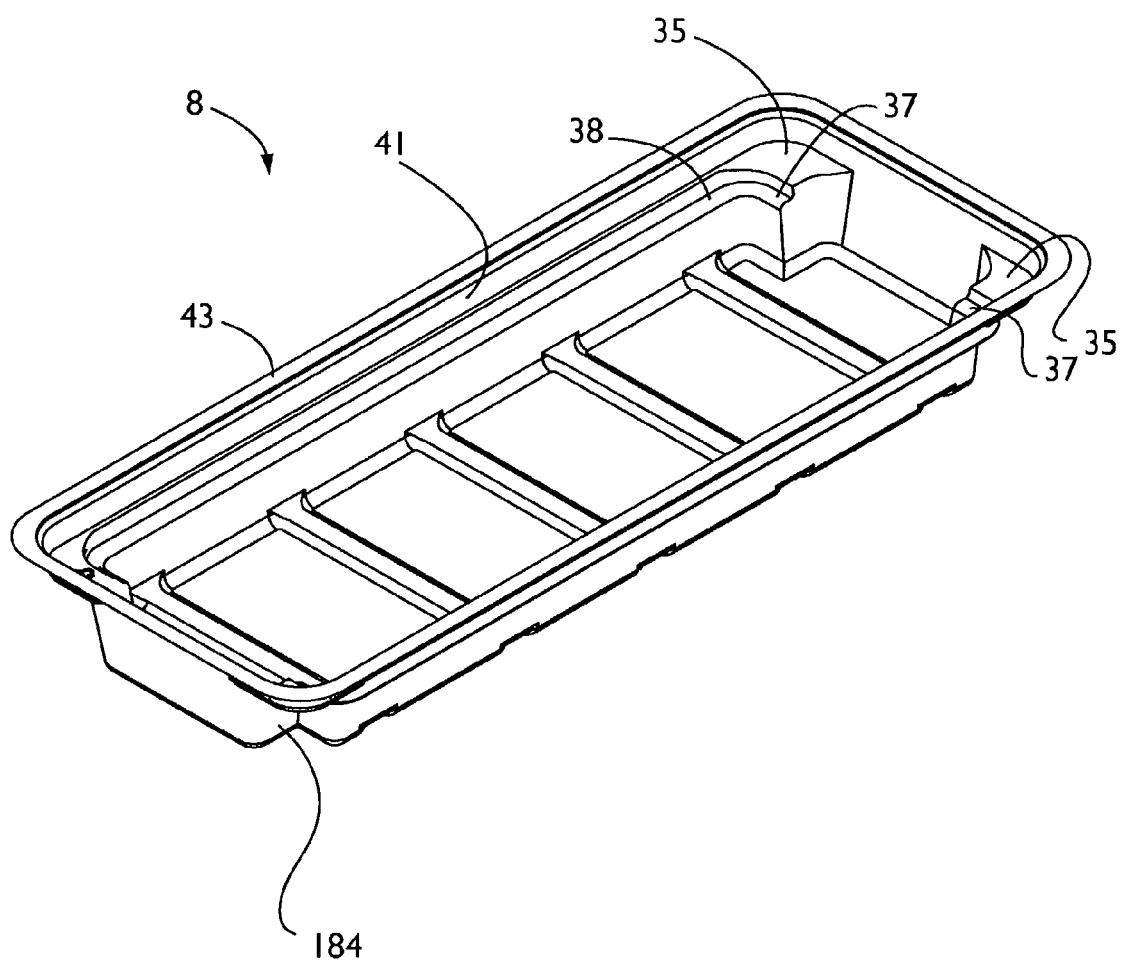
FIG. 4 is a perspective view of an outer shell that is a component of the functional package of FIG. 1.

Referring also to FIG. 4, the outer shell 8 is substantially rectangular, and a protrusion 36 is provided at or near each corner of the outer shell 8. Alternately, the outer shell 8 is shaped differently. Alternately, the protrusions 36 may be located in less than all corners of the outer shell 8, or in different positions in the outer shell 8. The protrusions 36 extend into an open space within the outer shell 8. Each protrusion 36 includes a depression 37 shaped to correspond to the shape of the lip 24 at each corresponding corner of the tray 4. The lip 24 of the tray 4 rests on one or more of the depressions 37. By holding the tray 4 at each of its corners, the tray 4 is supported and stabilized relative to the outer shell 8. The depressions 37 substantially prevent lateral motion of the lip 24 of the tray 4 relative to the outer shell 8. Alternately, the tray 4 may be held more securely at one or more of the depressions 37, such as by the use of clips, friction fitting, adhesive, or other structures, mechanisms or methods. Alternately, other or additional features may be provided in the inner surface of the outer shell 8 to hold the tray 4. The lip 36 of the tray top 6 is placed on the lip 24 of the tray 4, and is held in place by the depressions 37 in the same manner as the lip 24 of the tray 4. The depressions 37 are sized to receive and hold both lips 24, 36. The protrusions 35 form recesses 184 as viewed from outside the outer shell 8, and provide locations where the outer shell 8 can be easily gripped by a user.

One or more ridges 38 may be defined in the outer shell 8 in addition to the protrusions 36. If so, the lip 24 of the tray 4 may rest on the ridge or ridges 38 as well. Optionally, dimples (not shown) may be provided in a wall 41 of the outer shell 8 above the ridge or ridges 38. The lower surface of each dimple is positioned above a corresponding ridge 38 a distance substantially equal to the thickness of the lip 24 of the tray 4, in order to retain the tray 4 more securely within the outer shell 8. Thus, the tray 4 is snapped into place in the outer shell 8 over the dimples. Alternately, each dimple is positioned above a corresponding ridge 38 a distance substantially equal to the combined thickness of the lip 24 of the tray 4 and the lip 36 of the tray top 6, in order to retain both the tray 4 and the tray top 6 more securely. Optionally, the tray top 6 may include a grip 7 formed therein. The grip 7 is sized and shaped to allow a user to grasp it.

The cover 10 is bonded to the outer shell 8, such that the cover 10 seals the interior of the outer shell 8. The outer shell 8 may include a lip 43 extending outward from its perimeter, such that the cover 10 is sealed to the surface of the lip 43. The cover 10 may be fabricated out of TYVEK® brand protective material, a breathable, paper-thin material fabricated from olefin fibers. A different material capable of sealing the outer shell 8 may be used instead. The cover 10 is sealed to the outer shell 8 in such a way as to allow sterility to be maintained within the outer shell 8. Thus, the combination of the outer shell 8 and the cover 10 protect the tray 4 and tray top 6, allow them and the tools held within them to be sterilized and to remain sterile during storage, and provide a sterile interior even when the outer shell 8 is placed on a non-sterile surface.

The outer shell 8 and cover 10 may be placed in the exterior box 12. The exterior box 12 protects the outer shell 8 and cover 10 from outside elements during storage and during transportation to the surgery location. The exterior box 12 may be constructed from any material. The entire functional package 2 and its contents are sterilizable through the exterior box 12.

To begin preparation of a graft vessel for anastomosis, the exterior box 12 is opened, and the outer shell 8 and the cover 10 are slid out of it. The recesses 184 in the outer shell 8 provide locations at which the outer shell 8 can be gripped for removal from the exterior box 12. The outer shell 8 is placed upon a table or other surface in an operating room. The cover 10 is then removed from the outer shell 8. The tray 4 and tray top 6 then may be moved into the sterile field and the exterior box 12 and the cover 10 may be discarded. The tray top 6 is then removed and set aside or discarded, and the tray 4 is moved to a surgical table or other area near the patient. If the grip 7 is provided in the tray top 6, the user may grasp and pull it to separate the tray top 6 from the tray 4. The tray 4 and the tools within are then exposed and available for use.

The tray 4 is placed on a substantially flat surface such as a tabletop. The recesses 28, 30, 32 are shaped and positioned such that they rest on that substantially flat surface. When saline solution, blood or other biocompatible fluid is introduced into those recesses 28, 30, 32, the weight of that fluid holds the tray 4 against that surface. One or more stabilizing recesses 34 additionally may be provided in the tray 4. The stabilizing recesses 34 receive saline solution or other biocompatible fluid as well, such that the weight of that fluid holds the stabilizing recess 34 down and provides additional stability to the tray 4. Alternately, one or more of the recesses 28, 30, 32 do not contact the surface on which the tray 4 is placed. Alternately, none of the recesses 28, 30, 32 contact the surface on which the tray 4 is placed, and the tray 4 is stabilized solely by the use of stabilizing recesses 34. A graft vessel storage recess 42 optionally may be provided in the tray 4. Biocompatible fluid such as blood or saline is placed in the graft vessel storage recess 42, and the graft vessel for use in the anastomosis procedure is placed in that fluid in the graft vessel storage recess 42 until the appropriate time for preparing it. Alternately, where at least one stabilizing recess 34 is provided, a stabilizing recess 34 is used for storing the graft vessel before its preparation.

Figure 5:
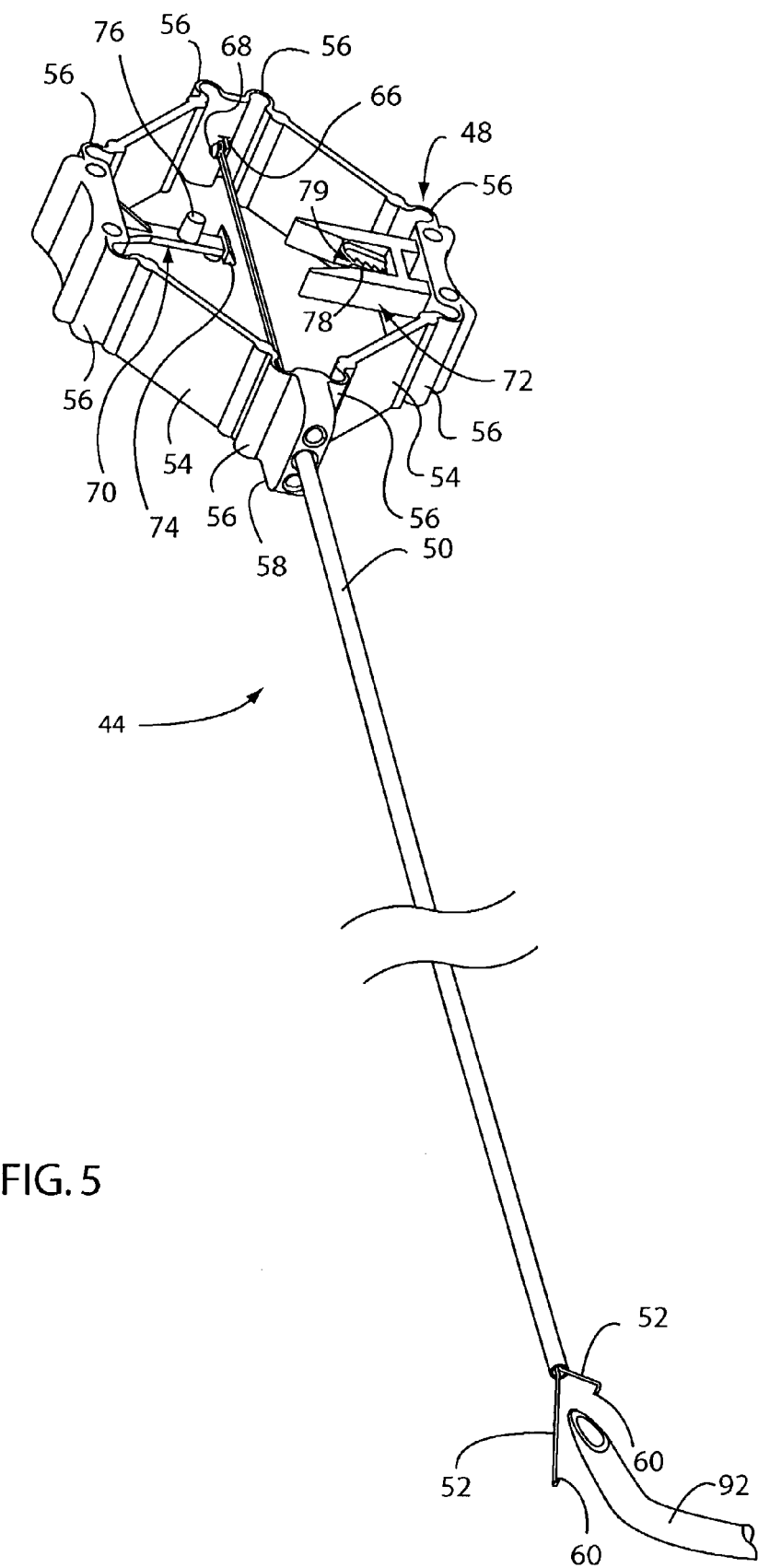
FIG. 5 is a perspective view of the pull-through tool in a first position.
Figure 6:
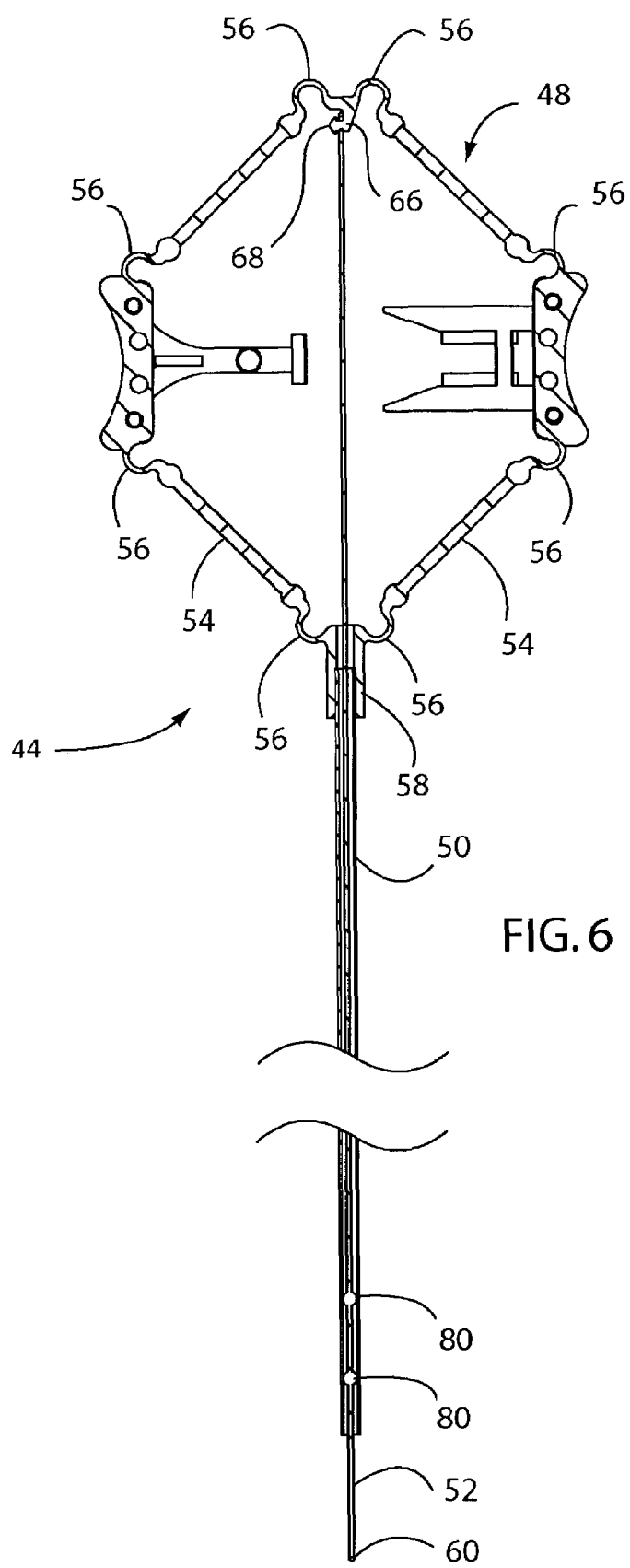
FIG. 6 is a cross-section view of the pull-through tool.
Figure 6A:
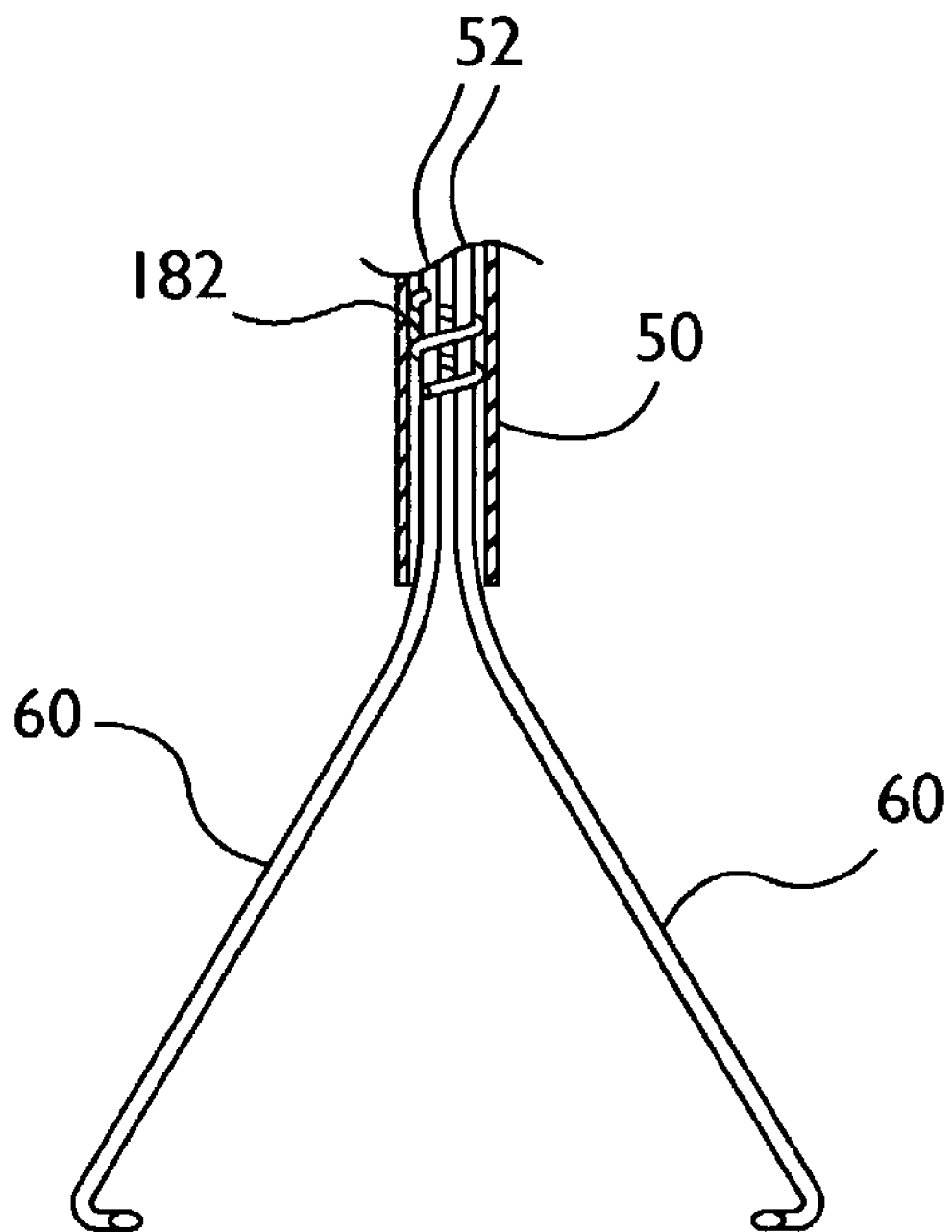
FIG. 6A is a cross-section view of the distal end of the pull-through tool.

Referring to FIGS. 3, 5 and 6, a pull-through tool 44 rests within the working recess 28 before it is used. The pull-through tool 44 may be interference-fit to the working recess 28 to substantially prevent its movement relative to the tray 4. Alternately, the pull-through tool 44 is loosely fit within the working recess 28. Alternately, the tray top 6 is shaped to restrain the pull-through tool 44 within the working recess 28. A stop 195 may be formed in or connected to the working recess 28. The stop 195 contacts the pull-through tool 44 and substantially prevents motion of the pull-through tool 44 in the direction of the stop 195. Referring also to FIG. 2B, a holding feature 202 optionally may be defined in or connected to the tray top 6. The holding feature 202 is positioned and/or shaped to assist in holding the pull-through tool 44 within the tray 4. For example, the holding feature 202 may be positioned on the tray top 6 such that it is adjacent to a handle 48 of the pull-through tool 44 when the pull-through tool 44 is placed in the working recess 28. In this way, the holding feature 202 prevents the pull-through tool 44 from moving past its position. As another example, the holding feature 202 may exert pressure on the pull-through tool 44 to press it into engagement with the working recess 28 and hold it substantially in place. The holding feature 202 may be shaped to conform to the shape of at least a portion of the pull-through tool 44, such as its handle 48, such that the holding feature 202 can better hold the pull-through tool 44 in place.

The pull-through tool 44 includes a handle 48 connected to a tube 50, through which at least one tension member 52 extends. The handle 48 includes two flexible members 54. The members 54 are connected to one another, directly or indirectly, at the proximal end and the distal end of the handle 48. The members 54 may be connected to one another at different or at additional locations. The tube 50 extends distally from the handle 48, and/or may extend between the members 54 of the handle 48. The flexibility of each member 54 of the handle 48 may be provided by one or more living hinges 56 that connect segments 57 of each member 54. Each segment 57 may be a thin, substantially rectangular structure. Alternately, the segments 57 may be shaped differently. The handle 48 is injection-molded plastic, such that the living hinges 56 are sufficiently strong and flexible to allow the members 54 to flex. The handle 48 may be constructed in a different manner or from a different material, if desired. Alternately, the handle 48 may be constructed from a compliant material, or made flexible in another manner. One or more segments 57 may include a grip 55 configured to be held by an operator. Each grip 55 is a structure curved to fit a human finger or thumb. Alternately, the grips 55 may be shaped differently.

The distal end of the handle 48 includes a collar 58 connected to and coaxial with the tube 50. Alternately, the collar 58 is located at a position on the handle other than its distal end. The members 54 may be connected to each other at their distal ends through connection with the collar 58. The tube 50 is also hollow, having a lumen therethrough. A lumen extends through the tube 50 and the collar 58. Alternately, the collar 58 is not used, and a hole or other passage is defined through the distal end of the handle 48 at or near the distal intersection of the members 54. The tube 50 is fixed to the collar 58. Alternately, the tube 50 is moveable relative to the handle 48. The tube 50 is constructed from a substantially flexible biocompatible material, such as polyethylene. Alternately, the tube 50 is not substantially flexible.

The handle 48 also includes a first arm 70 and a second arm 72, each connected to a different member 54. The arms 70, 72 are positioned relative to one another such that compression of the handle 48 moves them closer together. The first arm 70 is connected to one member 54 of the handle 48. The first arm 70 includes a ratchet pawl 74 at one end and a release element 76 on its surface. The ratchet pawl 74 and/or the release element 76 may be provided on other portions of the first arm 70, if desired. The ratchet pawl 74 is a wedge configured to mate with a corresponding element on the second arm 72, as described below. The ratchet pawl 74 may take another shape, if desired. The release element 76 is a protrusion or other structure connected to or formed into the first arm 70 in a direction substantially perpendicular to the first arm 70. The release element 76 may have a different angle relative to the first arm 70, if desired. The first arm 70 is configured to flex in a direction substantially perpendicular to the first arm 70, or in a different direction. The second arm 72 is connected to the other member 54. The second arm 72 includes one or more recesses 78 into which the ratchet pawl 74 of the first arm 70 can be received. The recesses 78 are provided on the underside of the second arm 72. Alternately, the recesses 78 are provided on a different surface of the second arm 72. A channel 79 extends substantially through the center of the second arm 72, providing a space through which the release element 76 can pass when the handle 48 is compressed. Alternately, the channel 79 is offset within the second arm 72. The recesses 78 are located on both sides of the channel 79, such that the ratchet pawl 74 can engage recesses 78 on both sides of the channel 79. Alternately, the channel 79 is not provided, where the release element 76 has a different configuration or is not used, or where the arms 70, 72 are configured differently.

Two tension members 52 are utilized. Alternately, a single tension member 52 is provided, having a split distal end including two or more grasping elements 60. Alternately, three or more tension members 52 may be used. Each tension member 52 is a wire constructed from stainless steel or other biocompatible material. Alternately, each tension member 52 may be constructed from a different material, or take a form other than a wire, such as a loop. The tension members 52 extend through the lumen of the tube 50. The proximal end of each tension member 52 is connected to the proximal end of the handle 48. The proximal end of the handle 48 may include a stud 66 to which the proximal end of each tension member 52 is fixed. More than one stud 66 may be provided, such that each tension member 52 is connected to a separate stud 66. The distal end of each tension member 52 extends out of the distal end of the tube 50. The distal ends of the tension members 52 are angled relative to the axis of the tube 50. A grasping element 60 is located at the distal end of each tension member 52. Alternately, the grasping element 60 is connected to a different location on the tension member 52. The distal end of each tension member 52 is bent to form the grasping element 60. A separate grasping element 60 may instead be connected to the distal end of each tension member 52. The grasping element 60 of each tension member 52 is oriented inward, toward the axis of the tube 50. Alternately, the grasping element 60 may be oriented at least partly in a different direction. One or more positioners 80 may be included on or connected to the tension members 52, each contacting and slidable relative to the inner surface of the tube 50, to facilitate motion of the tension members 52 through the tube 50. Optionally, referring also to FIG. 6B, a holder 182 is positioned substantially coaxial with the lumen of the tube 50. Advantageously, the holder 182 is located within the lumen of the tube 50 at or near its distal end. The holder 182 may be fixed to the tube 50 in any manner, such as by adhesive or by mechanical connection, or movable with respect to the tube 50. The holder 182 is a short coil spring. Alternately, the holder 182 may be a mechanism or structure other than a coil spring. The holder 182 has an opening or lumen therethrough. The tension members 52 extend through the opening in the holder 182. Because the lumen or opening through the holder 182 has a smaller diameter than the lumen of the tube 50, the tension members 52 are held more closely together at the location of the holder 182. Thus, when the holder 182 is located at or near the distal end of the tube 50, the holder 182 provides closer alignment for the grasping elements 60 as the tension members 52 are moved.

Figure 7:
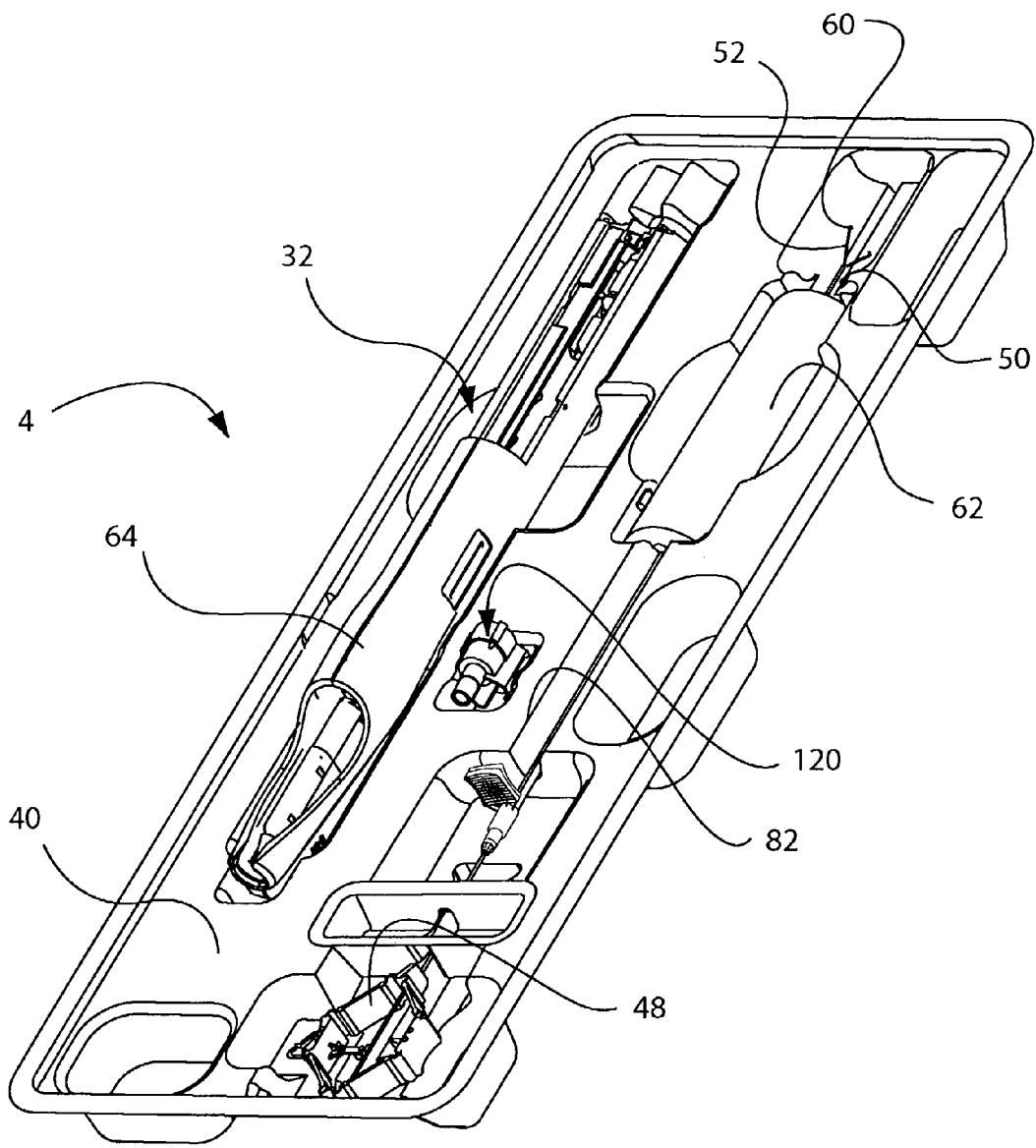
FIG. 7 is a perspective view of the tray of FIG. 2 in which a number of components are held.
Figure 8:
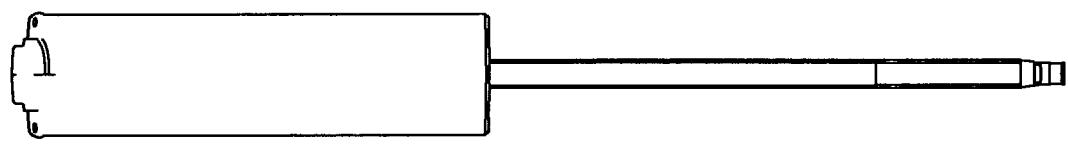
FIG. 8 is a side view of an assembly including a crown and an anastomosis device.
Figure 9:
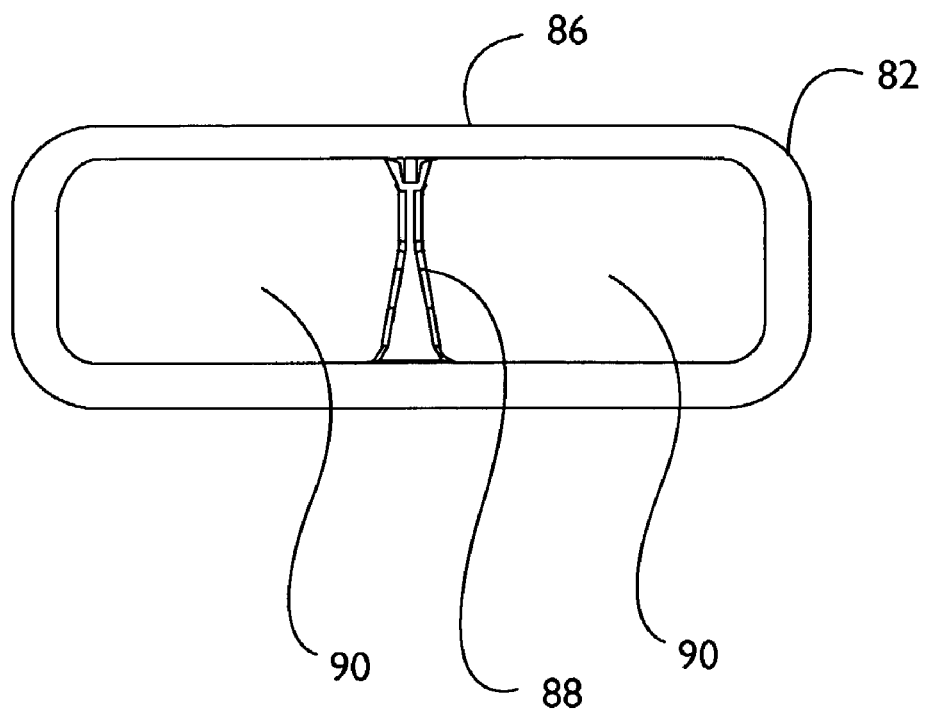
FIG. 9 is a top view of a stop clip that is detachably connectable to the tray.
Figure 10:
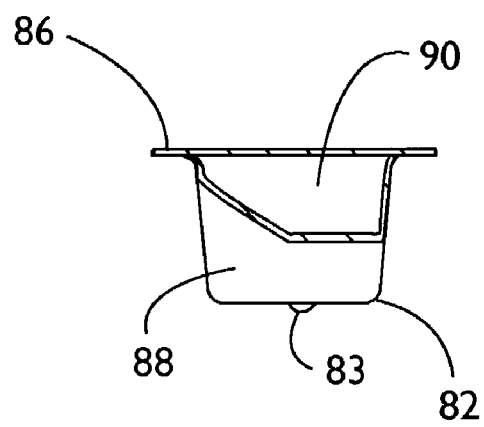
FIG. 10 is a side cross-section view of the stop clip of FIG. 9.

Referring also to FIGS. 7-8, an assembly 94 includes a cartridge 62, a crown 96, and an anastomosis device 98. An expander tube (not shown) is also included in the assembly 94, and is located partly within and coaxial with the crown 96, and partly within and coaxial with the anastomosis device 98. The crown 96 is an elongated member, such as a tube or a half-tube having two ends. One end of the crown 96 is slidably connected to the cartridge 62. The cartridge 62 is a component of an anastomosis tool 64, which is held in the anastomosis tool recess 32 of the tray 4. The cartridge 62 and the crown 96 may be a single piece that is molded or otherwise formed together. The crown 96 may extend through the entire cartridge 62, through part of the cartridge 62, or none of the cartridge 62. The cartridge 62 includes a lumen defined therethrough to receive the crown 96, the expander tube, and the tube 50 of the pull-through tool 44. The anastomosis device 98 is connected to the other end of the crown 96. This connection may be made by any structure, mechanism or method. The assembly 94 is held in a portion of the working recess 28. Alternately, a separate recess may be provided for the assembly 94. The assembly 94 may be friction-fit to the working recess 28 to substantially prevent its movement relative to the tray 4. Alternately, the assembly 94 is loosely fit within the working recess 28. Alternately, the tray top 6 is shaped to restrain the assembly 94 within the working recess 28. The assembly 94 is held in the tray 4 such that the tube 50 of the pull-through tool 44 extends into the expander tube within the crown 96 and out of the end of the cartridge 62 opposite to the crown 96. The working recess 28 is shaped to align the pull-through tool 44 and the assembly 94 such that the tube 50 can extend into the expander tube within the crown 96 while both are held in the tray 4.

Figure 2A:
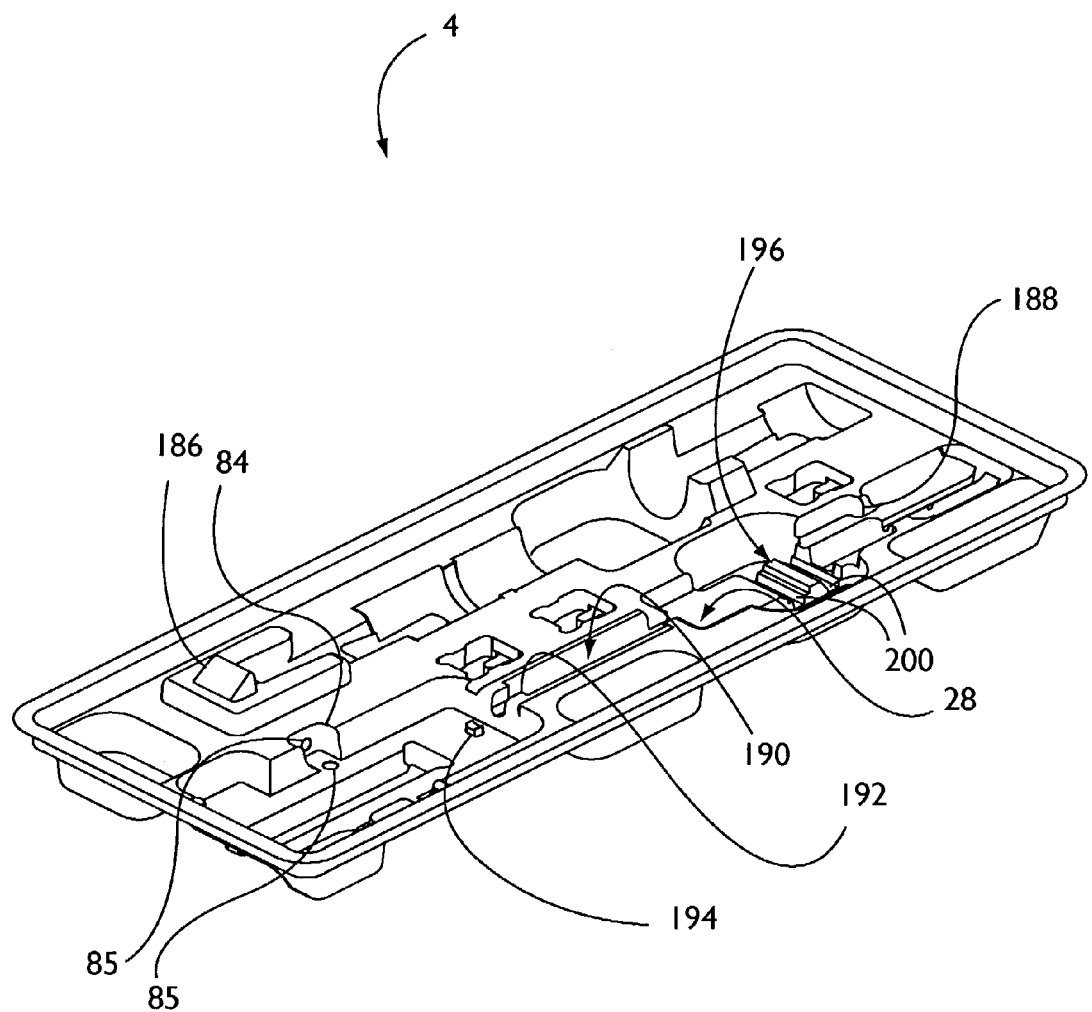
FIG. 2A is a perspective view of another embodiment of a tray that is a component of the functional package of FIG. 1.
Figure 2B:
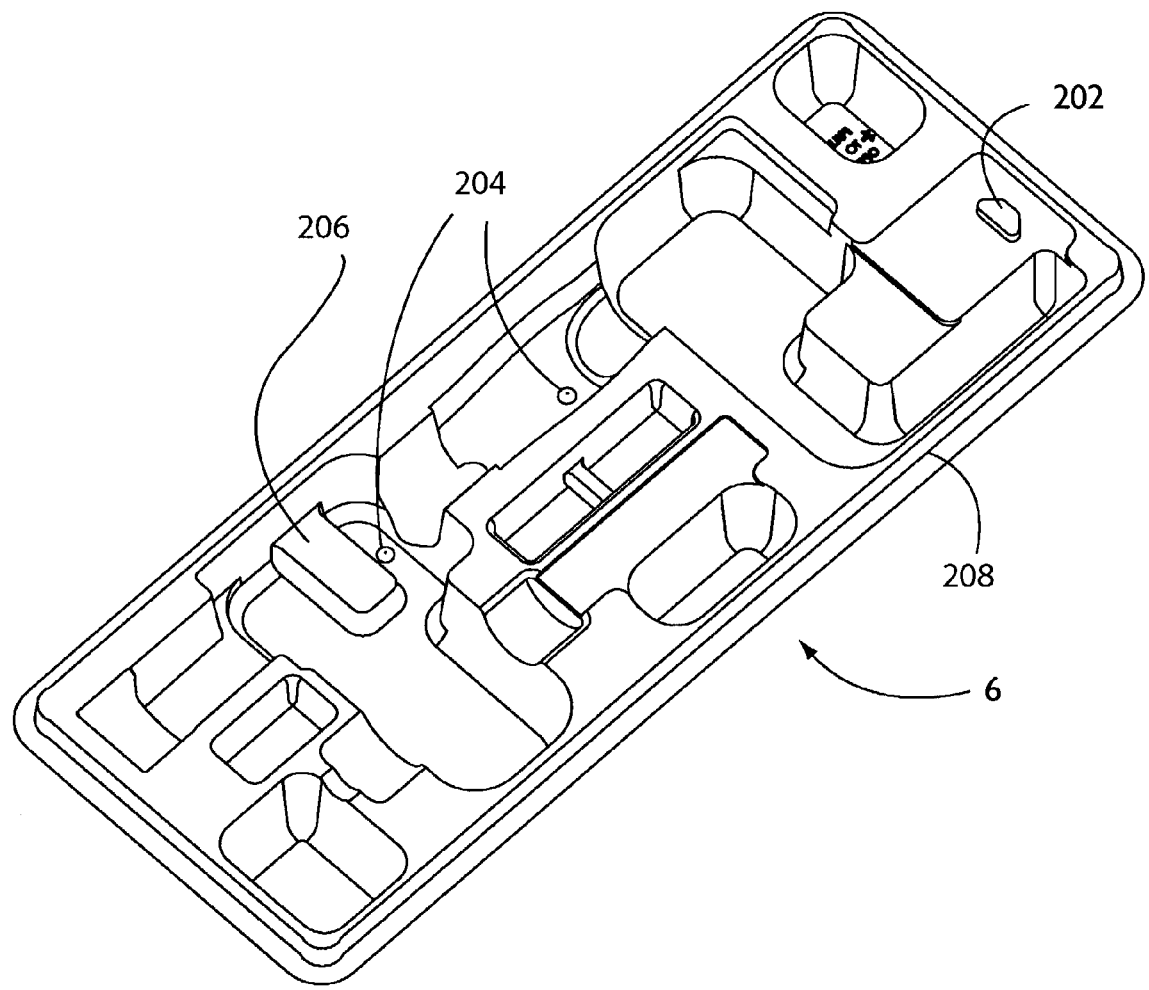
FIG. 2B is a perspective view of a tray top that is a component of the functional package of FIG. 1.

Referring also to FIG. 2A, the working recess 28 may include at least one restraining feature 196 defined therein or connected thereto. As shown, the restraining feature 196 includes laterally-extending troughs 200 defined in the surface of the working recess 28. The troughs 200 are configured to hold actuation features of the cartridge 62, such as but not limited to posts. Such posts may be as described in U.S. patent application Ser. No. 10/057,795, entitled "Integrated Anastomosis System," which is hereby incorporated by reference in its entirety. Such posts are movable relative to at least a portion of the cartridge 62, and their motion may act to deploy the anastomosis device 98. By holding the posts securely, the restraining feature 196 acts to prevent deployment of the anastomosis device 98 during shipping or motion of the package 2. Alternately, the restraining feature 196 and/or actuation features of the cartridge 62 may be configured differently. For example, more or fewer troughs 200 may be used. As another example, the troughs 200 may be shaped or oriented differently than described above, or from one another.

The anastomosis tool 64 is held within the anastomosis tool recess 32. The anastomosis tool 64 may be held substantially securely within the anastomosis tool recess 32, such as by a pressure fit. Referring also to FIG. 2B, the tray top 6 optionally may include one or more dimples 204 or other features defined in it or connected to it, oriented toward the anastomosis tool 64. Such dimples 204 press the anastomosis tool 64 against the anastomosis tool recess 32, substantially holding it in place by pressure. The anastomosis tool 64 may be held substantially securely within the anastomosis tool recess 32 in a different way, if desired.

As described in greater detail below, a clip 134 is connected to and detachable from the anastomosis tool 64. The tray top 6 optionally includes a ledge 206 defined therein or connected thereto. The ledge 206 is configured to engage the clip 134 and hold the clip 134 in place, such as by exerting pressure on the clip 134, or by blocking the motion of the clip 134 in one or more directions. The clip 134 may be held in place with additional, or different, structures and/or mechanisms if desired.

Referring also to FIG. 1A, a protection feature 186 may be provided in conjunction with the anastomosis tool recess 32. The anastomosis tool 64 has an operative end, which is positioned at a corresponding end of the anastomosis tool recess 32. In proximity to that end of the anastomosis tool recess 32, the protection feature 186 is formed in or connected to the tray 4. The operative end of the anastomosis tool 64 may include an auger, an anastomosis device or a portion thereof, or other sharp or delicate element or elements. The protection feature 186 is close enough to the anastomosis tool recess 32 and high enough such that it substantially prevents inadvertent contact with the operative end of the anastomosis tool 64. For example, the protection feature 186 extends to a distance above the surface 27 of the tray 4 that is at least as great as the distance between the operative end of the anastomosis tool 64 and the surface of the tray 4. The protection feature 186 may be configured differently, if desired.

Referring to FIGS. 7-10, a stop clip 82 is detachably connected to the tray 4. The stop clip 82 is pressure-fit into a depression 84 in the tray 4. However, the stop clip 82 may be connected to the tray 4 in another way. As one example, the stop clip 82 may be fixed to the tray 4, as with adhesive, or by molding the stop clip 82 and the tray 4 as a unit. The stop clip 82 includes a flange 86 that is fit against the surface of the tray 4 when the stop clip 82 is connected to the tray 4. The flange 86 may be omitted, if desired. Contact between the stop clip 82 and a ledge 208 on the tray top 6 may assist in holding the stop clip 82 in place in the depression 84.

The stop clip 82 includes a guide 88 that is wide enough to receive the tube 50 of the pull-through tool 44. The tube 50 may extend within the guide 88 while the pull-through tool 44 is held in the tray 4. Alternately, the guide 88 is above the tube 50 while the pull-through tool 44 is held in the tray 4. The guide 88 is sloped upward in the direction toward the handle 48 of the pull-through tool 44, and may widen in that direction as well. The stop clip 82 may also include two depressions 90, one on each side of the guide 88, where the guide 88 extends upward relative to the bottom surface of each depression 90. Referring also to FIG. 2A, the stop clip 82 optionally may include at least one registration feature 83, and the depression 84 includes a corresponding registration feature 85. As one example, the registration feature 83 on the stop clip 82 may be a convex bump, and the registration feature 85 in the depression may be a matching concave bump. However, the registration features 83, 85 may be formed differently. The registration features 83, 85 allow that the stop clip 82 to be placed in the depression 84 only in a position such that the guide 88 is oriented as described above. That is, the registration features 83, 85 ensure proper registration of the stop clip 82 with the depression 84. The tray top 6 optionally includes a feature 87 defined therein or connected thereto to assist in holding the stop clip 82 in place. This feature 87 may be a step, notch, bump or other feature that is configured to abut or otherwise interface with at least a portion of the stop clip 82, such as the flange 86. The feature 87 may apply pressure to the flange 86, or in another way hold the stop clip 82 in place or assist in holding it in place.

The pull-through tool 44 is moveable between a neutral configuration, in which the grasping elements 60 are separated from one another to receive a graft vessel, and an engaged configuration, in which the grasping elements 60 have moved together to engage the graft vessel. Initially, the pull-through tool 44 is in the neutral configuration as shown in FIG. 5. To operate the pull-through tool 44, a graft vessel 92 is removed from the graft vessel storage recess 42 of the tray 4 or otherwise obtained. The graft vessel 92 may be a vein graft such as a saphenous vein or a radial artery, as commonly used during a CABG procedure. However, the graft vessel 92 may be a tubular vessel other than one from the vasculature, and may be used in a surgery other than a CABG procedure. Advantageously, the end of the graft vessel 92 to be engaged by the pull-through tool 44 is cut at an angle on two opposite sides, in order to taper the graft vessel and facilitate its passage through the crown 96. The end of the graft vessel 92 may instead be cut substantially to its axis, or may not be cut at all. That end of the graft vessel 92 is held between the vein-grabbing elements 60 of the tension members 52 with forceps, by hand, or with a different tool. The operator of the pull-through tool 44 then begins to squeeze the handle 48. As the handle 48 is squeezed, the arms 70, 72 approach one another. Additionally, as the handle 48 is squeezed, the members 54 of the handle move closer to one another, and the length of the handle 48 increases. The proximal end of each tension member 52 is fixed to the proximal end of the handle 48, and the tension members 52 are slidable relative to the tube 50. As a result, the proximal end of the handle 48 pulls the tension members 52 proximally relative to the collar 58. Because the tube 50 is fixed to the collar 58, the tension members 52 thus move proximally relative to the tube 50 as well. The distal ends of the tension members 52 are angled relative to the axis of the tube 50. Thus, as the tension members 52 move proximally, they move into the tube 50, and contact between the angled distal ends of the tension members 52 and the tube 50 causes the tension members 52 to move closer to one another. Consequently, the grasping elements 60 move closer to one another.

Figure 5A:
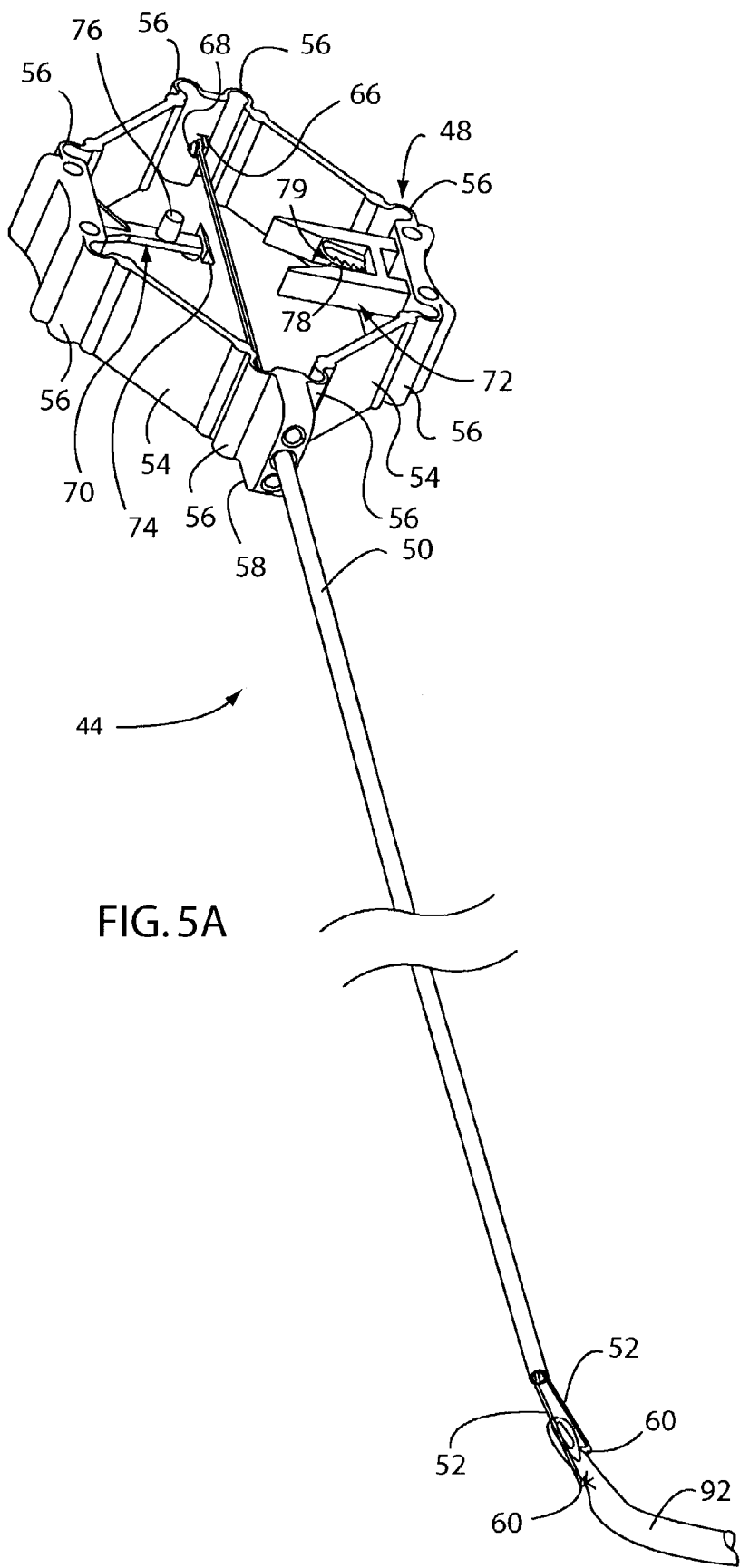
FIG. 5A is a perspective view of the pull-through tool in a second position.

Referring as well to FIG. 5A, as the handle 48 continues to be squeezed, the distance between the grasping elements 60 continues to decrease, and they engage the graft vessel 92 by penetrating it. Alternately, the grasping elements 60 may be configured to capture the graft vessel 92 without piercing or penetrating it. The arms 70, 72 are configured such that the ratchet pawl 74 of the first arm 70 encounters at least one recess 78 of the second arm 72 after the grasping elements 60 have moved to a position in which they are holding the graft vessel 92. The recesses 78 may be downwardly-extending spaces between teeth, or may be shaped differently. The first arm 70 is moveable in a direction perpendicular to its direction of motion toward the second arm 72, such that the ratchet pawl 74 can be deflected downward as the ratchet pawl 74 moves toward a recess 78, then deflect upward into a recess 78. The first arm 70 is configured to bias the ratchet pawl 74 into the recess 78 to secure the ratchet pawl 74 and recess 78 together when the grasping elements 60 have engaged the graft vessel. Recesses 78 may be provided at different distances from the first arm 70, such that the handle 48 can lock into a selected one of a number of different positions.

The graft vessel 92 is thus firmly held by the grasping elements 60 of the pull-through tool 44. The user then begins to pull the handle 48 of the pull-through tool 44 in a direction away from the assembly 94. In this way, the pull-through tool 44 begins to pull the graft vessel 92 through the lumen of the cartridge 62 and the crown 96. In order to pull the pull-through tool 44 in this direction, the handle 48 is lifted out of the working recess 28. The guide 88 of the stop clip 82 is shaped to allow the handle 48 to be moved away from the axis of the crown 96, and to control the motion of the tube 50 through the crown 96 to be substantially coaxial with the axis of the crown 96. The tube 50 is flexible, such that it bends based on its contact with the guide 88. The handle 48 continues to be moved away from the cartridge 62 until a portion of the graft vessel 92 is pulled out of the crown 96 adjacent to the anastomosis device 98 far enough to allow it to be cut with a scissors, scalpel or other tool. This cut is made between the anastomosis device 98 and the grasping members 60, thereby freeing the graft vessel 92 from the pull-through tool 44. The pull-through tool 44 and the portion of the graft vessel 92 retained by the grasping members 60 may then be discarded.

The release element 76 on the first arm 70 of the handle 48 can be used at any time during the operation of the pull-through tool 44 to release the graft vessel 92. By pressing on the release element 76, the first arm 70 is moved out of engagement with the recesses 78 of the second arm 72. The direction in which the release element 76 is pressed is substantially opposite to the direction in which the first arm 70 is biased. The handle 48 is then free to move back to its original, neutral configuration. Consequently, the tension members 52 move distally relative to the handle 48, and the grasping elements 60 once again move apart from one another, freeing the graft vessel 92. As an example of the use of the release element 76, an operator may utilize the release element 76 to free the graft vessel 92 if he or she is not satisfied with the security with which the grasping elements 60 have engaged the graft vessel 92.

Figure 11:
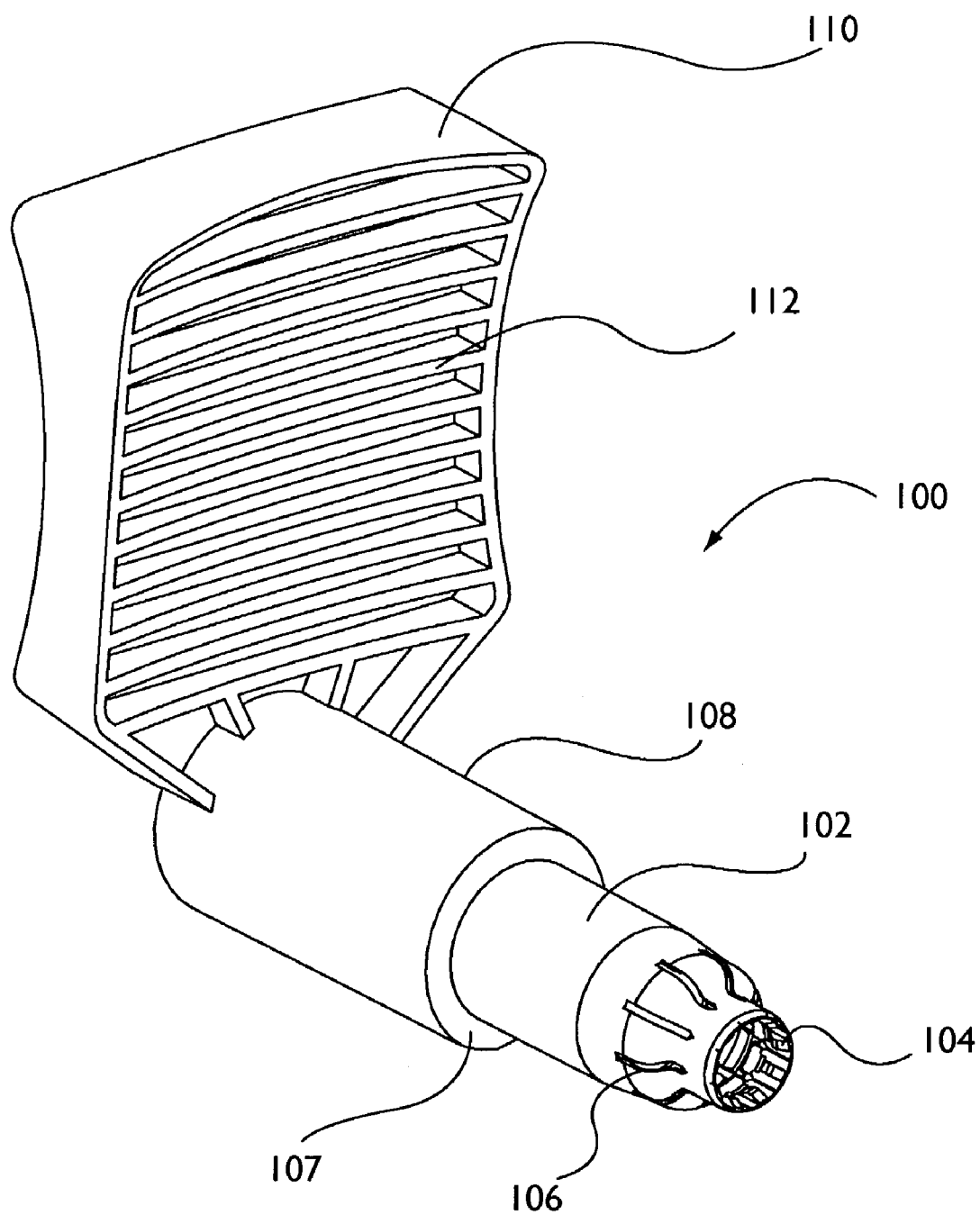
FIG. 11 is a perspective view of an eversion shield.
Figure 12:
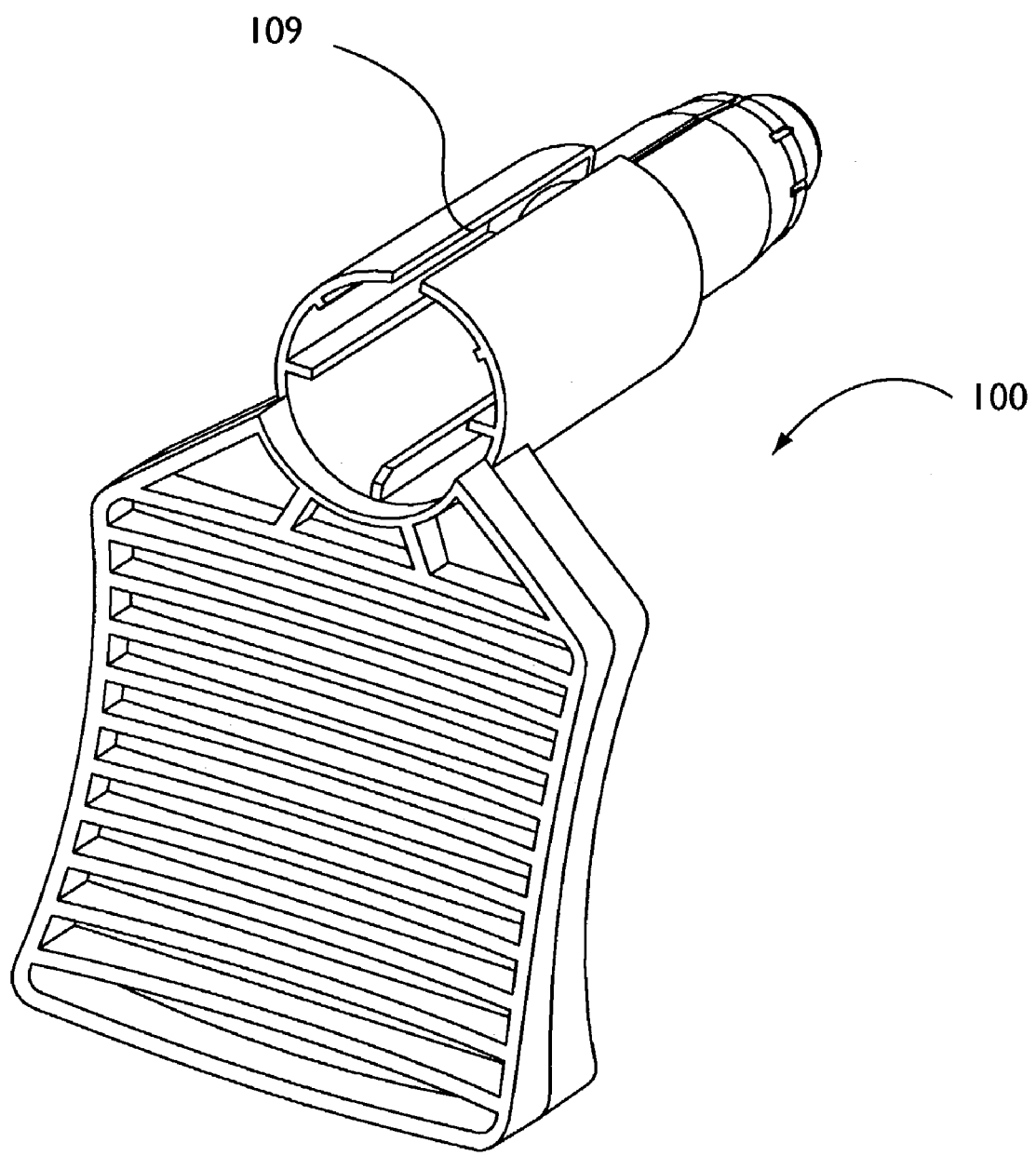
FIG. 12 is a different perspective view of the eversion shield of FIG. 11.

The anastomosis device 98 is positioned at one end of the crown 96. Referring to FIGS. 7 and 11-12, the anastomosis device 98 may include one or more tines 99 extending outward from it, at least partially in the direction of the axis of the crown 96. One or more tines 99 may extend in a different direction, if desired. An eversion shield 100 is placed over the anastomosis device 98, covering at least one of the tines 99, to facilitate eversion of the graft vessel 92. The eversion shield 100 is optional. If the eversion shield 100 is not used, the graft vessel 92 is everted over the anastomosis device 98 directly. The eversion shield 100 includes a substantially tubular body 102. The body 102 instead may be shaped differently. A barrier 104 is located at one end of the body 102. The barrier 104 is substantially tubular as well. The barrier 104 substantially encircles the tines 99 on the anastomosis device 98 and may contact them in whole or in part. The barrier 104 also extends further in the axial direction than the tines 99. Thus, the barrier 104 substantially covers the tines 99. The surface of the barrier 104 is substantially smooth, and the end of the barrier 104 is smoothed and/or finished to ensure that contact between the barrier 104 and the graft vessel 92 does not damage the graft vessel. The barrier 104 is open, allowing passage of the graft vessel 92 through it. The tines 99 are positioned in front of the anastomosis device 98. Thus, the barrier 104 may have a different diameter than the body 102 or taper to a narrower dimension than the body 102 in order to contact and cover the tines 99. Alternately, the barrier 104 may have substantially the same diameter as the body 102, depending on the configuration of the anastomosis device 98.

One or more slots 106 are positioned between the barrier 104 and the body 102. The slots 106 extend in a direction substantially parallel to the axis of the body 102, and are cut through the eversion shield 100. Alternately, the slots 106 do not extend entirely through the eversion shield 100. Alternately, the slots 106 extend in a different direction. The end of the body 102 opposite the barrier 104 may be connected to a secondary body 108 that is wider than the body 102. The secondary body 108 instead may be formed into the body 102. A tab 110 is connected to the secondary body 108 at or near the end of the secondary body 108 opposite from the body 102. Alternately, the tab 110 may be connected to another portion of the secondary body 108 or to the body 102, as long as its position does not interfere with the eversion of the graft vessel 92. The tab 110 is sized to be graspable by a user. The tab 110 may include ribs 112 or other features to enhance the user's grip upon the tab 110.

Figure 13:
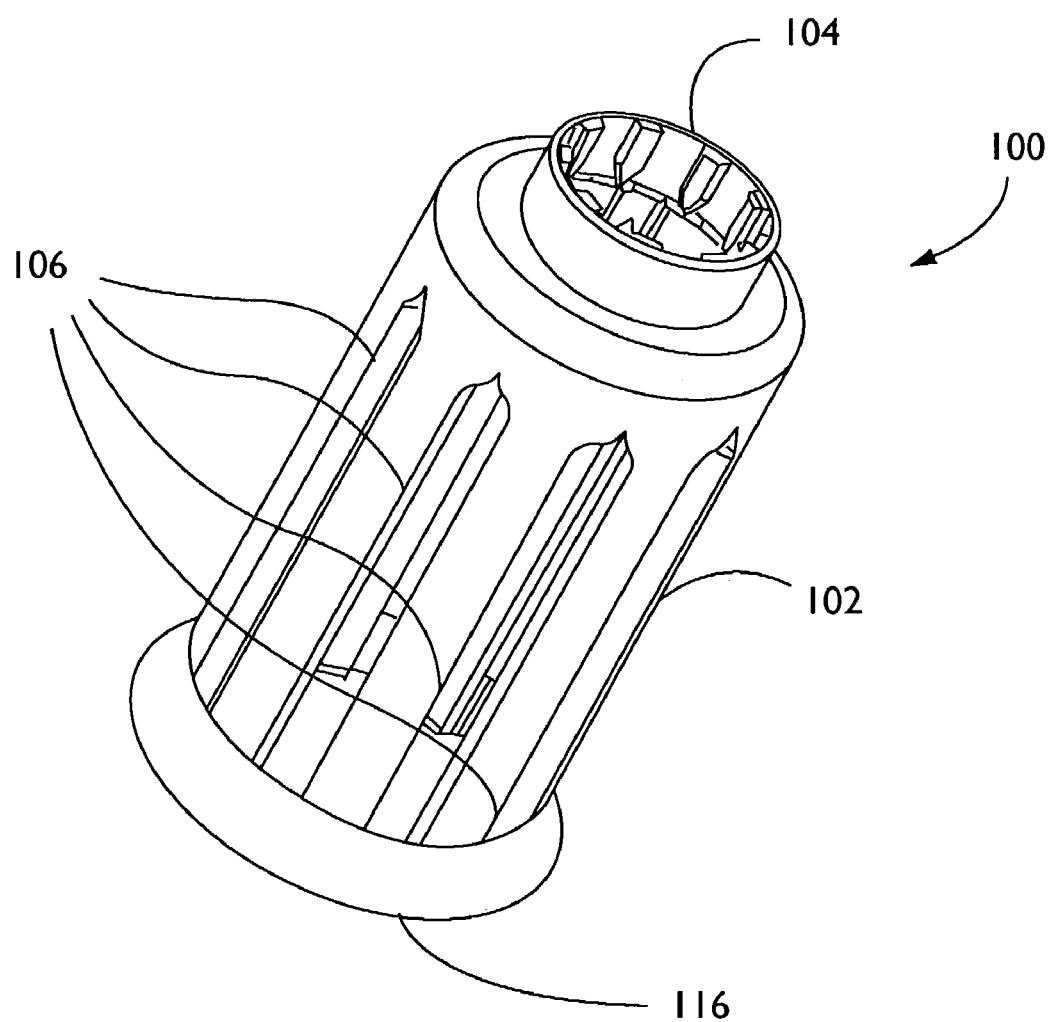
FIG. 13 is a perspective view of an alternate eversion shield.
Figure 14:
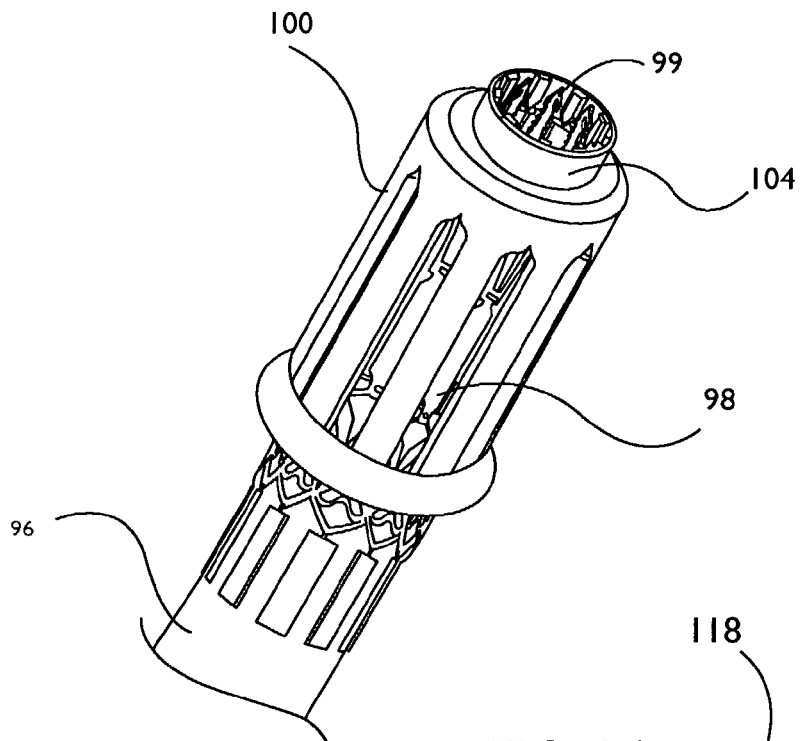
FIG. 14 is a perspective view of the eversion shield of FIG. 13 covering an anastomosis device.
Figure 15:
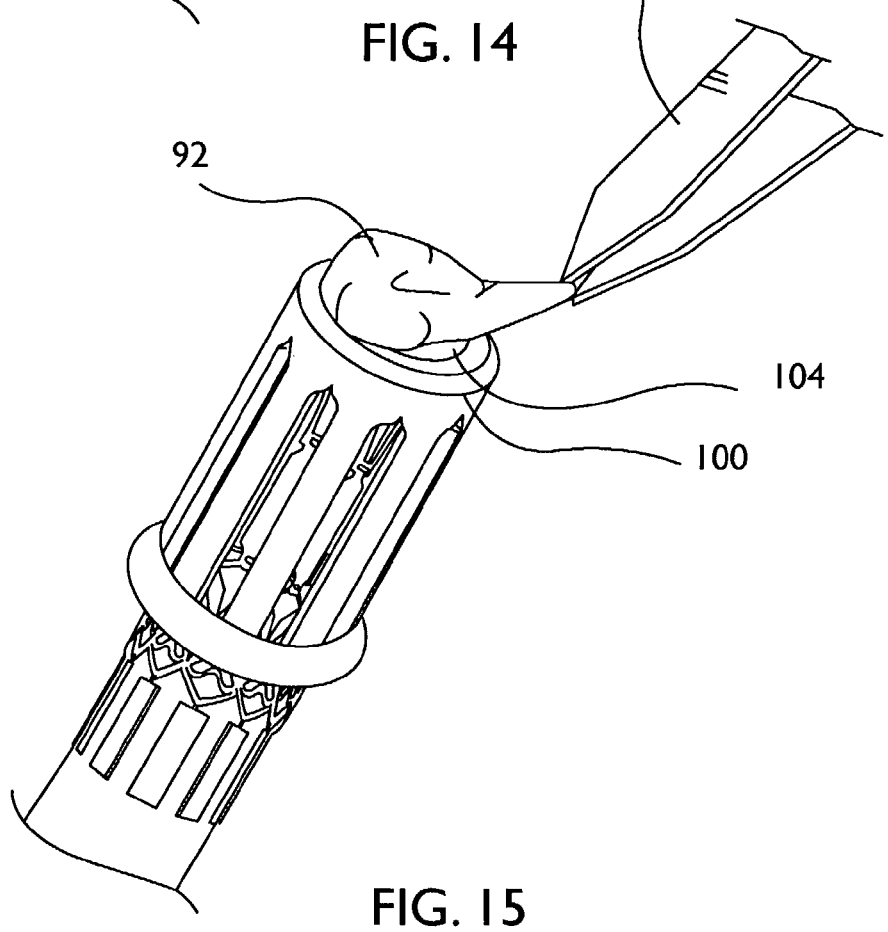
FIG. 15 is a perspective view of the eversion shield of FIG. 13 illustrating the eversion of a graft vessel over the eversion shield.

As another example of an eversion shield 100, referring to FIGS. 13-15, at one end of the eversion shield 100 the barrier 104 is positioned to cover at least one of the tines 99, as described above. The eversion shield 100 includes a body 102 connected to the barrier 104. The body 102 is substantially tubular, but may be shaped differently if desired. One or more slots 106 are cut through the body 102 in a direction substantially parallel to the axis of the body 102. The slots 106 may be cut in a different direction, if desired. At the end of the body 102 opposite from the barrier 104 is a stop 116. The slots 106 extend substantially as far as the stop 116. Alternately, the slots 106 do not extend as far as the stop 116. The stop 116 is a ring having a diameter larger than the diameter of the body 102. The stop 116 instead may be shaped differently.

Referring particularly to FIG. 15, a person utilizes one or more forceps 118 or other tools to evert the end of the graft vessel 92 over the barrier 104. Two or more people may work together to perform the eversion, if desired. The graft vessel 92 is everted across the single substantially smooth end of the barrier 104 and onto the outer surface of the barrier 104. Eversion over the smooth end and surface of the barrier 104 is simpler than eversion over one or more tines 99. Further, the amount of eversion can be adjusted after the end of the graft vessel has been everted over the barrier 104, because the graft vessel 92 can slide over the smooth end of the barrier 104 without being damaged.

Figure 16:
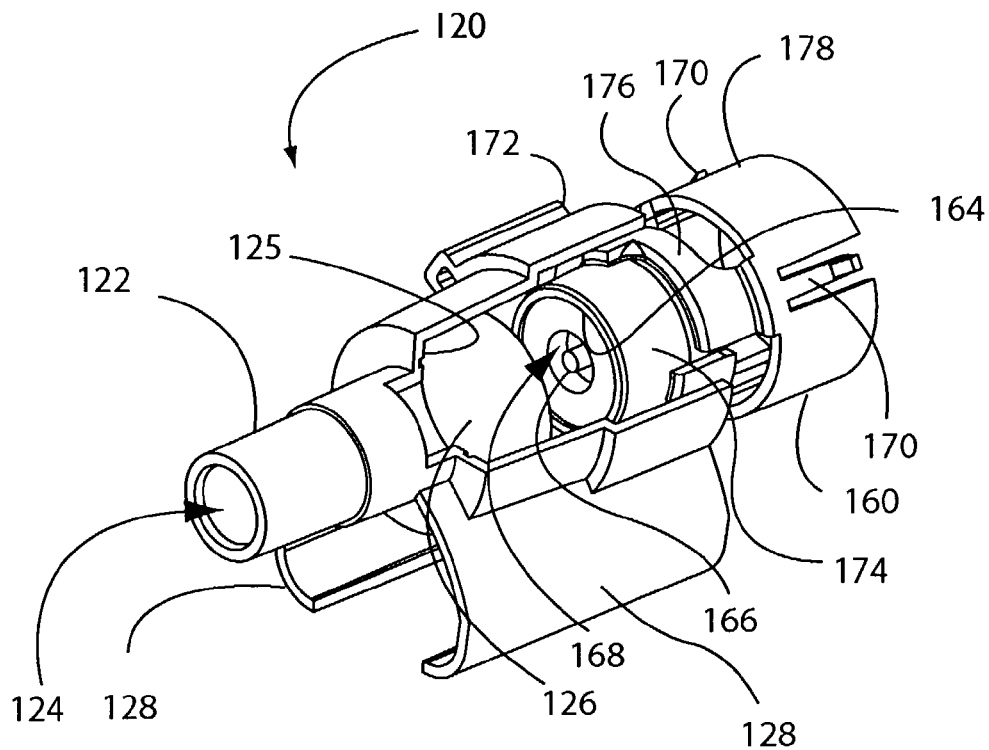
FIG. 16 is a cutaway exploded view of the poke-through tool.
Figure 17:
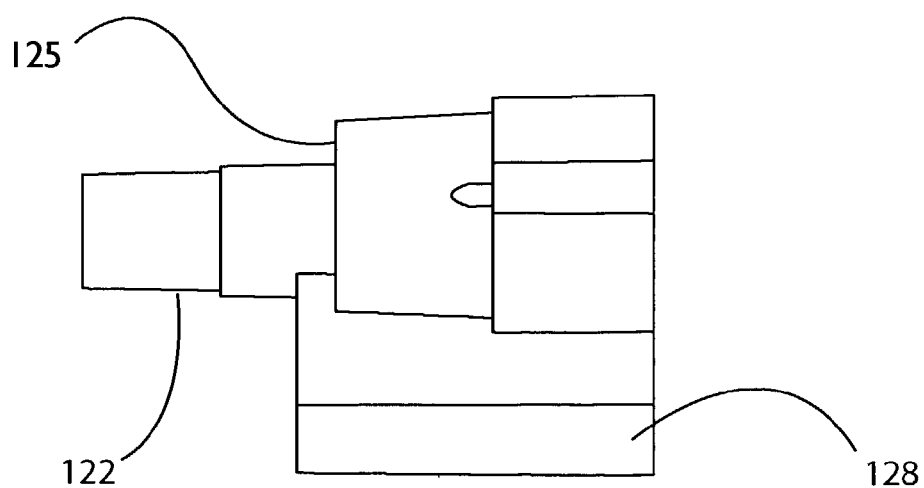
FIG. 17 is a side view of the poke-through tool.

After the graft vessel 92 has been everted over the barrier 104, the eversion shield 100 is removed and the tines 99 are poked through the graft vessel 92. Referring to FIG. 7, a poke-through tool 120 is held in the poke-through tool recess 30. Referring also to FIGS. 16-17, the poke-through tool 120 includes three primary components: a shell 122, a membrane 126, and a tensioning member 160. The shell 122 has an opening 124 at one end that is large enough to be slid over the anastomosis device 98. The shell 122 includes a shoulder 125, where the diameter of the shell 122 increases from a first diameter to a second, larger diameter. The first diameter of the shell 122 is near the opening 124, and the second diameter is further from the opening 124. The shell 122 may be shaped differently, such that the shoulder 125 is present at the location at which the area enclosed by a perpendicular cross-section of the shell 122 increases. A membrane 126 is connected to the shell 122 at the shoulder 125.

The membrane 126 is made of polyester film, and is substantially 1 mil (0.001) inches thick. However, the membrane 126 may be made of any other appropriate material or combination of materials, and/or have a different thickness. For example, the membrane 126 may be a screen or a net. As another example, the membrane 126 may be a rigid member, such as a stainless steel disk, having holes therethrough corresponding to the tines 99 of the anastomosis device 140. Alternately, other structures, mechanisms or methods may be provided in lieu of the membrane 126.

The tensioning member 160 includes a drum 174 connected by spring members 176 to a base 178. The drum 174 is sized and shaped to contact the membrane 126, tension it, and hold it in place. The shoulder 125 includes a substantially circumferential groove 162 defined therein. Alternately, the groove 162 may extend in a different direction, or multiple, smaller grooves or notches may be used. A ridge 164 is defined at the end of the drum 174 that contacts the membrane 126. The ridge 164 is shaped and sized to correspond to the groove 162, such that axial force applied to the tensioning member 160 causes the ridge 164 to press a portion of the membrane 126 into the groove 162, holding it in place and tensioning it. Thus, the membrane 126 is substantially flat where the tines 99 contact it. A post 166 is located substantially at the axial centerline of the tensioning member 160, at the end of the drum 174 that contacts the membrane 126. A trough 168 at least partially surrounds the post 166.

Figures 17A, 17B:
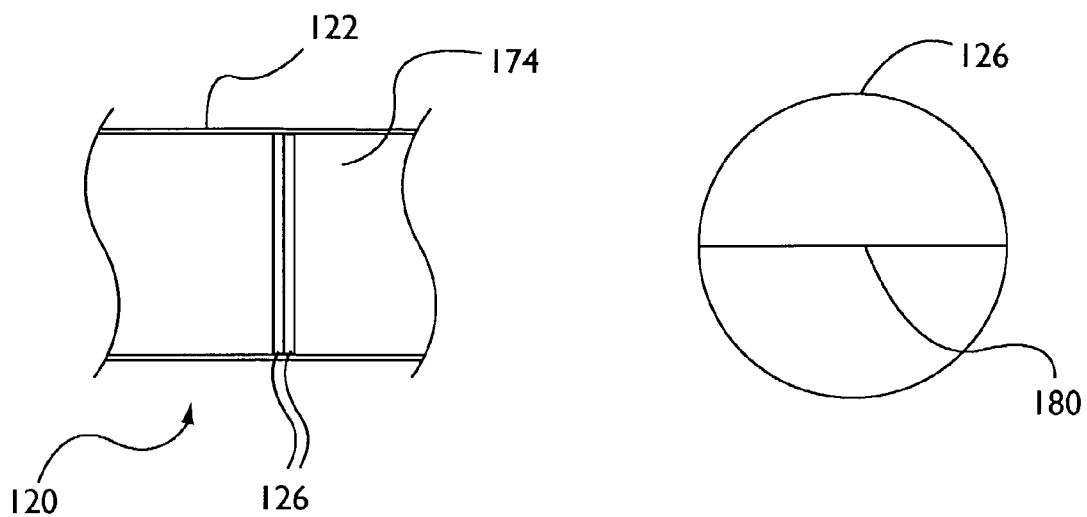
FIG. 17A is a detail cutaway view of a plurality of membranes within the poke-through tool.
FIG. 17B is an end view of a membrane usable within the poke-through tool, the membrane having a reference mark thereon.

Referring to FIG. 17A, a plurality of membranes 126 may be included in the poke-through tool 120. At least two of these membranes 126 may contact one another. This contact may be over all or part of the adjacent surfaces of the membranes 126. Alternately, at least two of the membranes 126 may be spaced apart from one another. The use of multiple membranes 126 provides redundancy in the event that penetration of one membrane 126 does not completely push down the graft vessel 92. Advantageously, two membranes 126 are used. More may be utilized, if desired. A plurality of membranes 126 are used, rather than a single thicker membrane 126, because additional force is required to penetrate the tines 99 through a thicker membrane. Alternately, a thicker single membrane 126 may be used. Where multiple membranes 126 are used, all of them need not be composed of the same material.

Figure 17C:
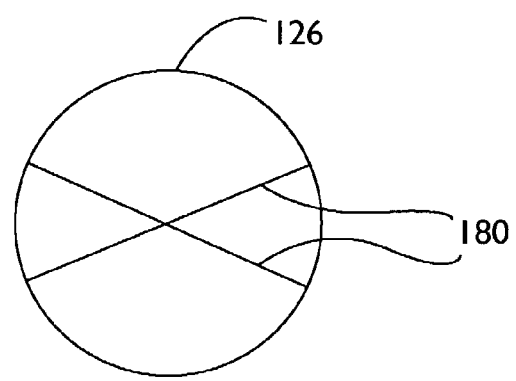
FIG. 17C is a end view of two membranes aligned with one another, each membrane having a reference mark thereon.

Referring also to FIG. 17B, at least one membrane 126 optionally includes a reference mark 180. The reference mark 180 may be a substantially straight line that substantially bisects the membrane 126. Alternately, the reference mark 180 is configured differently. The reference mark 180 may be defined on the surface of the membrane 126 with ink, dye or a different substance, embedded in the material of the membrane 126, or otherwise associated with the membrane 126. Referring also to FIG. 17C, when a plurality of membranes 126 are included in the poke-through tool 30, the reference marks 180 on the different membranes 126 can be seen to intersect or otherwise overlap when viewed through the opening 124 of the shell 122. The references marks 180 are useful in inspecting the poke-through tools 30 during and/or after their fabrication. By ensuring that the reference marks 180 intersect substantially at an expected location, the alignment of the membranes 126 can be confirmed. For example, where the reference mark 180 bisect the corresponding membranes 126, and the reference marks 180 intersect substantially at an expected location, such as the axial centerline of the shell 122, it can be determined that none of the membranes 126 have been mounted off-center in the poke-through tool 120.

To provide additional redundancy, multiple poke-through tools 120 may be packaged in the tray 4. Each poke-through tool 120 is held in a separate poke-through recess 30. Alternately, more than one poke-through tool 120 may be held in a single poke-through recess 30.

One or more flexures 170 are provided on the base 178 of the tensioning member 160, configured to engage mating structures 172 defined in the shell 122. Such engagement connects the tensioning member 160 to the shell 122, and axially compresses the spring members 176. This axial compression acts against the membrane 126 and the shoulder 125 to hold the membrane 126 in place and tension it. Other structures, mechanisms or methods than flexures 170 may be used to connect the tensioning member 160 to the shell 122. Further, other structures, mechanisms or methods may be used to exert a substantially axial force on the membrane 126 to hold it in position and to tension it.

The poke-through tool 120 also includes one or more sliders 128 extending from the shell 122. Referring also to FIG. 3, the sliders 128 are sized to fit into and slide within a channel 130 located in the working recess 28. The channel 130 is a substantially rectangular depression having a substantially rectangular cross-section in the working recess 28. Alternately, the channel 130 may have a different shape or cross-section. The channel 130 has a centerline that is substantially parallel to the axis of the crown 96. The sliders 128 are sized to place the shell 122 substantially coaxial with the crown 96. Thus, motion of the poke-through tool 120 along the channel 130 causes the shell 122 to move substantially coaxially relative to the crown 96. The sliders 128 are curved structures extending from the shell 122, shaped to substantially prevent lateral movement or angular movement of the poke-through tool 120 relative to the axis of the crown 96. Alternately, one slider 128 is used, having a substantially rectangular shape substantially as wide as the channel 130. Alternately, the slider or sliders 128 have a different shape. Any shape or number of sliders 128 may be used that substantially prevent lateral movement or angular movement of the poke-through tool 120 relative to the axis of the crown 96.

In operation, the poke-through tool 120 is removed from the poke-through tool recess 30. The sliders 128 of the poke-through tool 120 are placed in the channel 130 in the working recess 28, with the opening 124 of the shell 122 facing the anastomosis device 98. The poke-through tool 120 is then slid toward the anastomosis device 98 along the channel 130. The shape of the channel 130 and its contact with the sliders 128 substantially prevents rotation of the poke-through tool 120 during its translation relative to the anastomotic device 98. As the poke-through tool 120 moves toward the anastomosis device 98, the anastomosis device 98 enters the opening 124 in the shell 122. The graft vessel 92 has been everted over the anastomosis device 98, as described above. The membrane 126 contacts the everted graft vessel 92 at a point in the translation of the poke-through tool 120. The motion of the membrane 126 forces the graft vessel 92 onto the tines 99, causing the tines to poke through the graft vessel 92. The tips of the tines 99 then contact the membrane 126, penetrating it and entering the trough 168. This penetration may make a sound, providing auditory confirmation that the tines 99 have pierced the membrane 126. Where multiple membranes 126 are used, the tips of the tines 99 contact each membrane 126 in turn before entering the trough 168. The post 166 supports the membrane or membranes 126 against the forces that result from contact between the tines 99 and the membrane or membranes 126. The poke-through tool 120 continues to translate in the same direction, such that at least one membrane 126 pushes the graft vessel 92 down onto the tines 99 of the anastomosis device 98. The channel 130 is sized and positioned such that motion of the poke-through tool 120 along the entire length of the channel ensures that the poke-through tool 120 has pushed the graft vessel onto the tines 99 a preselected amount. That is, the length of the channel 130 controls the amount of translation of the poke-through tool 120. Alternately, the anastomosis device 140 and the assembly 94 are movable relative to one another. Alternately, the poke-through tool 120 is fixed relative to the tray 4, and the assembly 94 is movable relative to it. As an example, the poke-through tool 120 may be formed into the tray 4, and the working recess 28 is configured to allow the assembly 94 to slide toward the poke-through tool 120.

Figure 18:
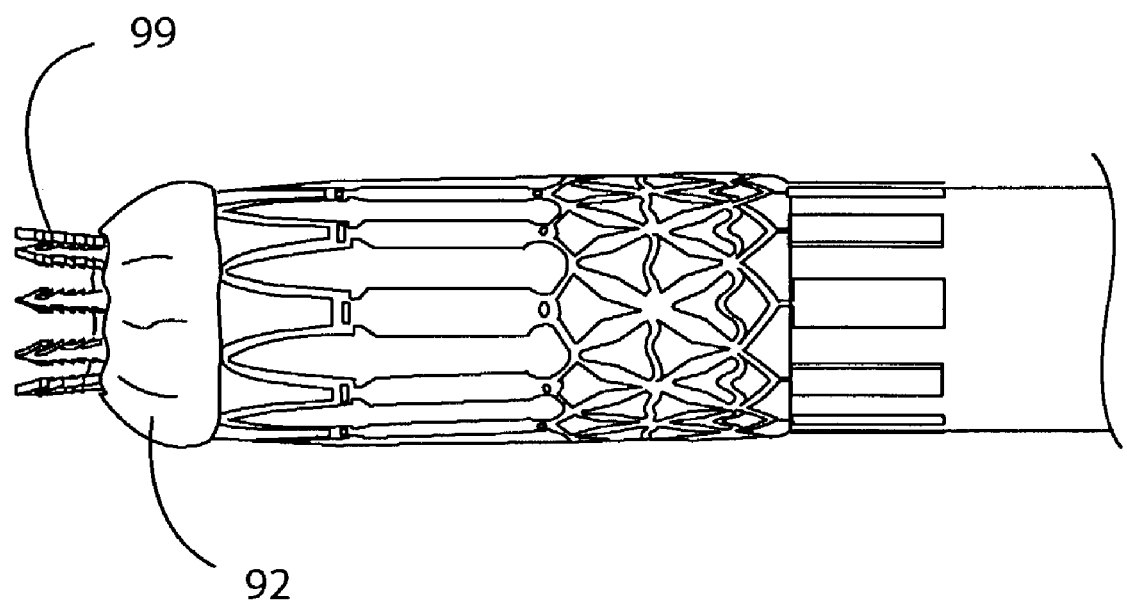
FIG. 18 is a perspective view of the graft vessel relative to the anastomosis device after the poke-through tool has pushed the graft vessel through the tines of the anastomosis device.

Referring also to FIG. 2A, a stop 188 may be defined in or connected to the tray 4 within the working recess 28, adjacent to or in proximity to the cartridge 62. The stop 188 is positioned such that it limits or substantially prevents motion of the cartridge 62 in response to force exerted by the poke-through tool 120 on the anastomosis device 98; such force is transmitted through the crown 96 to the cartridge 62. The stop 188 may be shaped or configured in any appropriate manner. For example, the stop 188 may include two protrusions extending laterally into the working recess 28, each from a side wall thereof, with a space between them through which the tube 50 of the pull-through tool 44 can be passed. Alternately, the stop 188 is not used, and the cartridge 62 is held substantially in place in another way while the poke-through tool 120 is used. The poke-through tool 120 is then moved in the opposite direction along the channel 130, away from the anastomosis device 98. The end result is shown in FIG. 18, where the graft vessel 92 has been pushed down onto the tines 99.

Referring also to FIGS. 11-12, if the eversion shield 100 is used, the poke-through tool 120 also cooperates with the eversion shield 100 to release the eversion shield 100 from the crown 96 and/or anastomosis device 98. As the poke-through tool 120 moves relative to the crown 96, a portion of the poke-through tool 120 contacts the shoulder 107 between the body 102 and the secondary body 108 of the eversion shield 100. Because the barrier 104 has a smaller diameter than the shoulder 107, the eversion shield 100 resists motion in the direction of the motion of the poke-through tool 120. Additionally, the poke-through tool 120 may stress the shoulder 107 via direct contact. Further attempted motion of the poke-through tool 120 relative to the eversion shield 100 in the same direction thus results in a force on the eversion shield 100. This force results in stress within the eversion shield 100. This stress acts to extend the slots 106 in the direction toward the poke-through tool 120 and split one end of each slot 106 open relative to the end of the eversion shield 100 nearest the poke-through tool 120. The shape of the slots 106 and the thickness and composition of the body 102 are selected to result in such splitting upon this stress. After the slots 106 have split open, the width of the barrier 104 is no longer a constraint on the motion of the eversion shield 100, which is free to move relative to the crown 96, away from the anastomotic device 98. Referring to FIG. 12, the eversion shield 100 includes a split 109 on one surface to allow it to be removed from the crown 96 entirely. The split 109 extends along the body 102 and secondary body 108 of the eversion shield 100, such that the body 102 and secondary body 108 can flex as the eversion shield 100 is pulled from the crown 96 in a direction substantially perpendicular to the axis of the crown 96.

Figure 19:
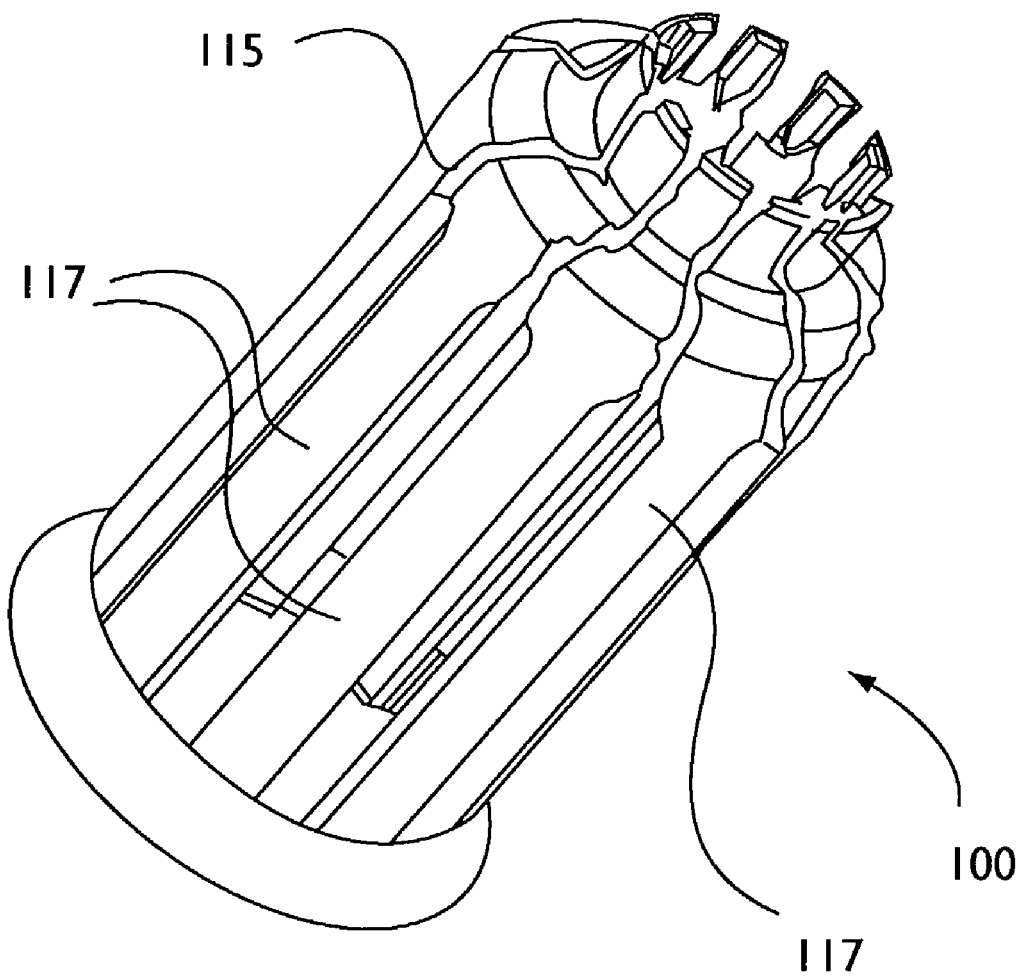
FIG. 19 is a perspective view of the eversion shield of FIG. 13 after the poke-through tool has split it for removal.

Similarly, the poke-through tool 120 also cooperates with the eversion shield 100 as shown in FIGS. 13-15. The poke-through tool 120 encounters the stop 116 as the poke-through tool 120 is moved toward the anastomosis device 98. Because the barrier 104 has a smaller diameter than the anastomotic device 98 and the crown 96, the eversion shield 100 resists motion in the direction of the motion of the poke-through tool 120. Further attempted motion of the poke-through tool 120 relative to the eversion shield 100 in the same direction thus results in a force on the eversion shield 100. This force results in stress within the eversion shield 100. Referring also to FIG. 19, this stress acts to extend the slots 106 in the direction toward the poke-through tool 120 and split one end of each slot 106 open relative to the end of the eversion shield 100 nearest the poke-through tool 120. The shape of the slots 106 and the thickness and composition of the eversion shield 100 are selected to result in such splitting upon this stress. Further, the shape of the slots 106 is chosen such that fracturing and tear propagation begins at the end 115 of each slot 106. After the slots 106 have split open, the width of the barrier 104 is no longer a constraint on the motion of the eversion shield 100. The freed eversion shield 100 is then pushed behind the everted portion of the graft vessel 92, away from the anastomotic device 98, such that individual elements 117 formed by the fracturing of the eversion shield 100 splay outward at an angle to the axis of the eversion shield 100. The eversion shield 100 can thus be safely slid forward over the everted portion of the graft vessel 92, and removed from the crown 96. Alternately, the eversion shield 100 may be constructed to be removable from the anastomotic device 98 and/or the crown 94 without contacting the poke-through tool 120. Alternately, a tool other than the poke-through tool 120 may be used to remove the eversion shield 100 from the anastomotic device 98 and/or the crown 94.

The graft vessel 92 is then ready for an anastomotic procedure. The pull-through recess 28 is filled with saline or other biocompatible fluid to a depth such that the prepared graft vessel 92 held on the assembly 94 is substantially immersed in that fluid until needed. Thus, the graft vessel 92 can be prepared before or while a surgeon or other medical professional prepares the patient and/or performs other tasks preparatory to the anastomotic surgery. In this way, the tray 4 not only holds a number of tools 44, 100, 120 used for preparing the graft vessel 92, but also provides a sterile retaining area in which the graft vessel 92 can be immersed after being prepared. The working recess 28 is deep enough to hold biocompatible fluid up to a level covering the crown 96 and the prepared graft vessel 92. When the crown 96 is covered with fluid, the expander tube within is located below the fluid level as well. Thus, the assembly 94 is held within the working recess 48 while one or more tools, such as the pull-through tool 44 and the poke-through tool 120, are moved relative to and/or interface with the assembly 94 in order to prepare the graft vessel 92. The assembly 94 and the attached graft vessel 92 are held within the working recess 48 until the surgeon is ready to perform anastomosis.

When the surgeon is ready to perform anastomosis, the assembly 94 is removed from the biocompatible fluid within the working recess 28 and connected to the anastomosis tool 64. Referring also to FIG. 2A, the working recess 28 includes a crown recess 190, where the crown 96 rests. The crown 96 may be held in place in the working recess 28 by a neck 192 within the crown recess 190, where the neck 192 has a smaller cross-sectional area than the rest of the crown recess 190. The neck 192 may be located at or near one end of the crown recess 190, or at a different location in the crown recess 190. More than one neck 192 may be utilized. The crown 96 is pressure-fit into the neck 192, to substantially restrain the motion of the crown 96 and of the assembly 94 as a whole as it rests in the tray 4. As the user removes the assembly 94 from the working recess 28, he or she applies adequate force to overcome the pressure fit between the crown 96 and the neck 192. The neck 192 is shaped relative to the crown 96 such that the force required to remove the crown 96 is larger than forces exerted on the package 2 in transit, and low enough that the assembly 94 can be removed easily from the working recess 28 without tools.

A support 194 is located on a surface of the working recess 28 that is between an end of the crown recess 190 and the location underneath the position of the anastomosis device 98. Thus, the support 194 is positioned substantially underneath the portion of the crown 96 that extends out of the crown recess 190. The support 194 is a bump or other feature extending at least partially upward from the surface of the working recess 28. As the crown 96 and the rest of the assembly 94 are removed from the crown recess 190, the assembly 94 may tilt such that the crown 96 contacts the support 194. If so, the support 194 supports the crown 96 as the two come into contact, holding the crown 96 above the bottom of the working recess 28. Further, the height of the support 194, and its location relative to the crown recess 190, are chosen such that the anastomosis device 98 at the end of the crown 96 is held above the bottom of the working recess 28, protecting it against contact with the tray 4 as the assembly 94 is removed from the working recess 28.

Figure 20:
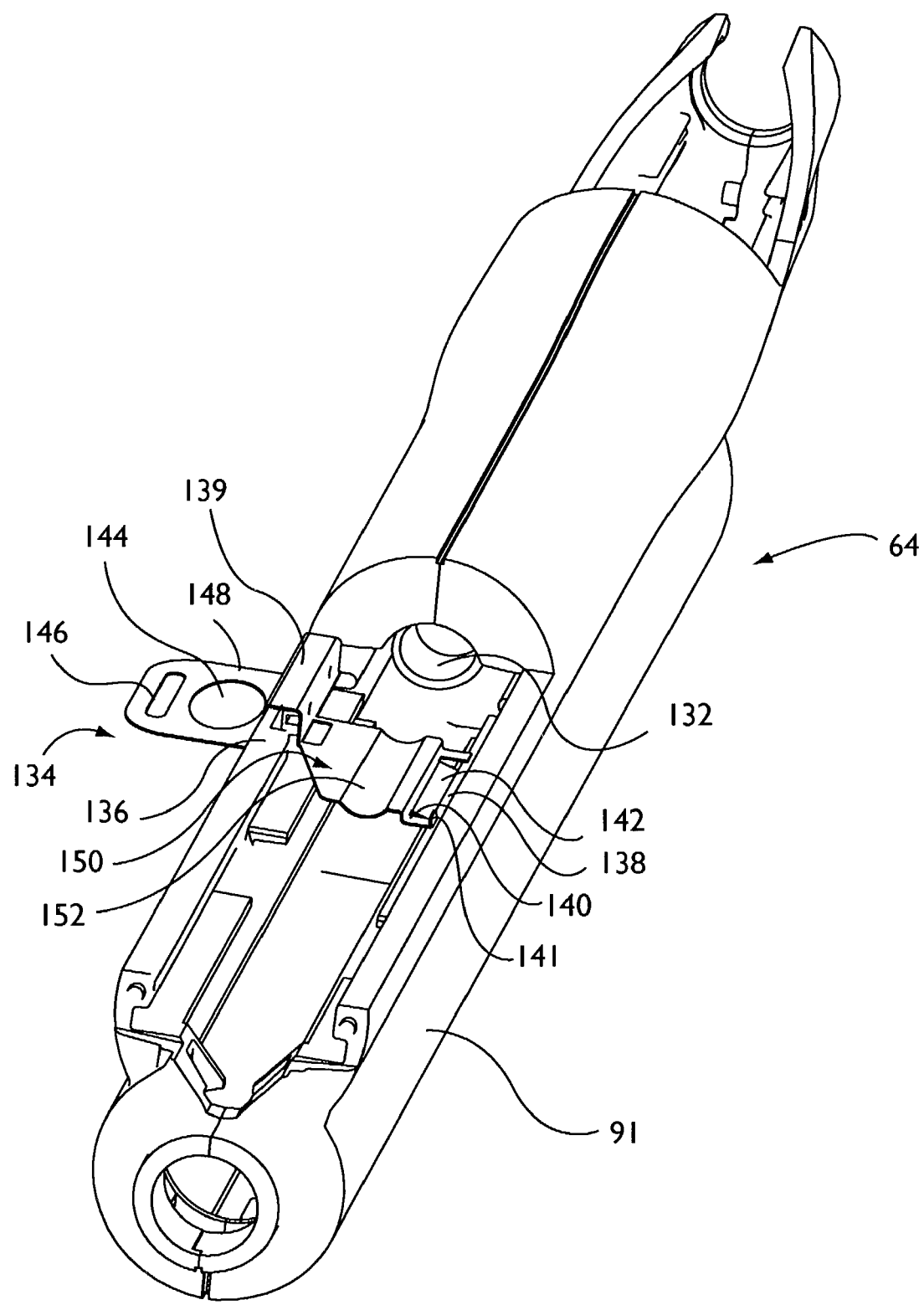
FIG. 20 is a perspective view of an anastomosis tool and a guide used therewith.
Figure 21:
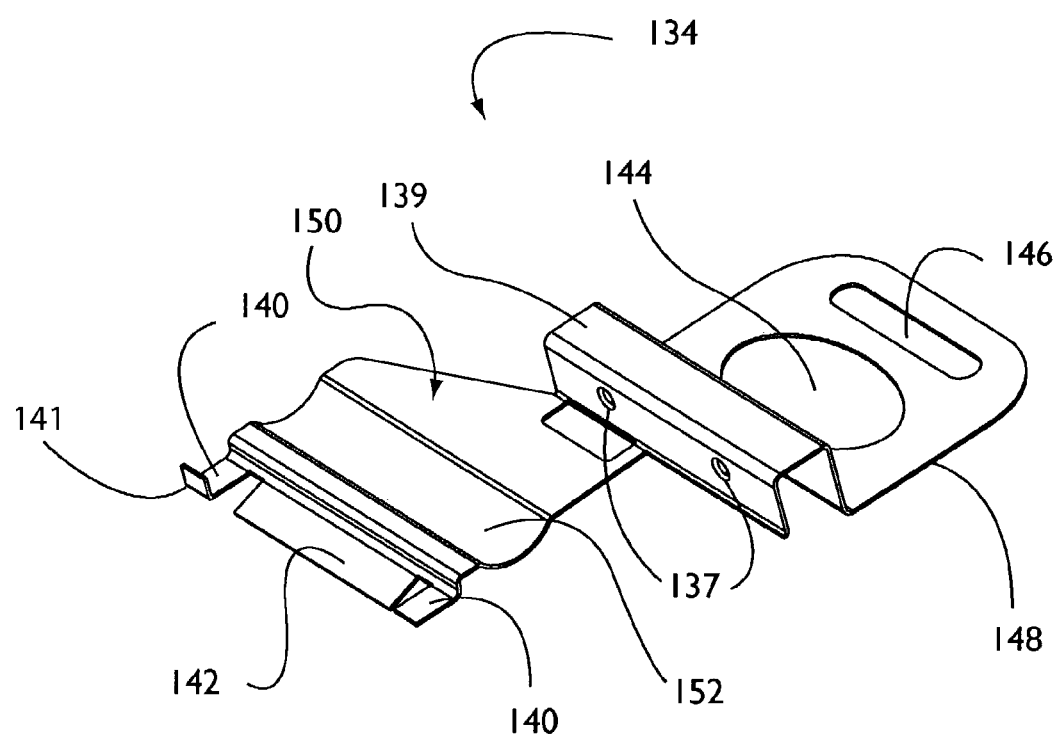
FIG. 21 is a perspective view of the guide of FIG. 20.

Referring to FIGS. 20-21, the anastomosis tool 64 includes a passage 132 therethrough with a diameter large enough to receive the crown 96, expander tube, anastomosis device 98 and graft vessel 92. The anastomosis tool 64 includes at least one edge 136 for mating with the cartridge 62, and may include one or more flanges 138. A clip 134 is connected to and detachable from the anastomosis tool 64. The clip 134 includes an indented feature 139 configured to fit onto the edge 136. This fit may be a pressure fit, facilitated by indentations 137 in the feature 139 oriented toward the edge 136 of the anastomosis tool 64. Alternately, the clip 134 is connected to the edge 136 and/or at least one flange 138, or to another portion of the anastomosis tool 64, in a different way. Alternately, the indented feature 139 may be configured to fit onto a different structure on the anastomosis tool 64. The clip 134 may be constructed from plastic, polycarbonate, stainless steel, or any other appropriate material.

The clip 134 includes tabs 140, 142 configured to fit onto one of the flanges 138. Two tabs 140 fit over the flange 138, and one tab 142 fits under the flange 138. Structures other than or in addition to the tabs 140, 142 may be used to connect the clip 134 to at least one flange 138 and/or to another structure. A stop 141 extends upward from the proximal tab 140. The clip 134 includes a paddle 148 extending away from the anastomosis tool 64. The paddle 148 includes a grip feature 144 that an operator can grasp or otherwise engage. The paddle 148 may be an indentation, hole, or other feature. The paddle 148 may also include a passage 146 through which a strap or other retainer (not shown) may be inserted. Alternately, the passage 146 is not used, and the strap or other retainer passes through the grip feature 144.

The clip 134 includes a platform 150 that extends between the indented feature 139 and the tabs 140, 142. The platform 150 includes an indentation 152. The indentation 152 has an arcuate cross-section that is aligned with the passage 132 in the anastomotic tool 64. The indentation 152 is shaped to guide the crown 96 into the passage 132. Thus, the indentation 152 is shaped to have a radius of curvature similar to the crown 96. Alternately, the indentation 152 may have a different shape or radius of curvature. By sliding the crown 96 along the indentation 152, the crown 96 enters the passage 132 in proper alignment with the passage 132. When the cartridge 62 contacts the stop 141 or comes close to contacting the stop 141, the clip 134 is removed from the anastomosis tool 64, and the assembly 94 is moved to its final position relative to the anastomosis tool 64. The tool 64 is then ready for use.

While the invention has been described in detail, it will be apparent to one skilled in the art that various changes and modifications can be made and equivalents employed, without departing from the present invention. For example, the tools and functional package described above may be used for surgical procedures other than CABG procedures, such as peripheral vascular surgery, neurovascular surgery, or transplant surgery. It is to be understood that the invention is not limited to the details of construction and/or the arrangements of components set forth in the above description or illustrated in the drawings. Therefore, the invention is not to be restricted or limited except in accordance with the following claims and their legal equivalents.

What is claimed is:

1. A poke-through tool for use with a graft vessel connected to an anastomosis device having tines, the tool comprising:
    at least one membrane configured to impart a force to at least a portion of the graft vessel; and
    a shell with an opening therein, said shell having an interior, wherein said membrane is positioned within said interior of said shell.

2. The poke-through tool of claim 1, wherein said force is oriented to push at least a portion of the graft vessel relative to the tines.

3. The poke-through tool of claim 1, wherein said membrane is tensioned.

4. The poke-through tool of claim 1, comprising a plurality of membranes, wherein at least two said membranes contact one another.

5. The poke-through tool of claim 4, wherein at least one said membrane includes at least one reference mark defined thereon.

6. The poke-through tool of claim 5, wherein said reference mark is a line on said membrane.

7. The poke-through tool of claim 5, wherein said reference mark substantially bisects said membrane.

8. The poke-through tool of claim 1, comprising a plurality of membranes, wherein at least two said membranes are spaced apart from one another.

9. The poke-through tool of claim 1, wherein said membrane is composed of polyester film.

10. The poke-through tool of claim 1, further comprising at least one slider attached to said shell.

11. The poke-through tool of claim 1, further comprising a tensioning member connected to said shell and to said membrane.

12. The poke-through tool of claim 11, wherein said tensioning member is a drum.

13. A method for preparing a graft vessel for anastomosis, comprising:
    providing a membrane and an anastomosis device having tines;
    associating said anastomosis device with the graft vessel by everting an end of the graft vessel about said tines; and
    moving said anastomosis device and said membrane relative to one another such that a portion of the graft vessel is pressed between said membrane and said anastomosis device.

14. The method of claim 13, further comprising tensioning at least one said membrane prior to said moving.

15. The method of claim 12, wherein said tines penetrate at least one said membrane during said moving.

* * * * *

UNITED STATES PATENT AND TRADEMARK OFFICE
CERTIFICATE OF CORRECTION

PATENT NO. : 7,427,261 B1 Page 1 of 1
APPLICATION NO. : 10/426838
DATED : September 23, 2008
INVENTOR(S) : Carranza et al.

It is certified that error appears in the above-identified patent and that said Letters Patent is hereby corrected as shown below:

In the title of the patent, item (54); "CRAFT" should read --GRAFT--.

Column 18, line 40, that portion of dependent claim 15 reading "claim 12" should read --claim 13--.

Signed and Sealed this

Eighteenth Day of November, 2008

JON W. DUDAS
*Director of the United States Patent and Trademark Office*

UNITED STATES PATENT AND TRADEMARK OFFICE
CERTIFICATE OF CORRECTION

PATENT NO.        : 7,427,261 B1                                    Page 1 of 1
APPLICATION NO.   : 10/426838
DATED             : September 23, 2008
INVENTOR(S)       : Carranza et al.

It is certified that error appears in the above-identified patent and that said Letters Patent is hereby corrected as shown below:

In the title of the patent, item (54) and Column 1, line 1; "CRAFT" should read --GRAFT--.

Column 18, line 40, that portion of dependent claim 15 reading "claim 12" should read --claim 13--.

This certificate supersedes the Certificate of Correction issued November 18, 2008.

Signed and Sealed this

Ninth Day of December, 2008

JON W. DUDAS
*Director of the United States Patent and Trademark Office*